US00RE44648E

(19) United States
(12) Reissued Patent
Amin et al.

(10) Patent Number: US RE44,648 E
(45) Date of Reissued Patent: Dec. 17, 2013

(54) ENZYME FOR THE PRODUCTION OF LONG CHAIN PERACID

(75) Inventors: Neelam S. Amin, Palo Alto, CA (US); Richard R. Bott, Palo Alto, CA (US); Marguerite A. Cervin, Palo Alto, CA (US); Ayrookaran J. Poulose, Palo Alto, CA (US); Walter Weyler, Palo Alto, CA (US)

(73) Assignee: Danisco US Inc., Palo Alto, CA (US)

(21) Appl. No.: 13/507,300

(22) Filed: Jun. 15, 2012

Related U.S. Patent Documents

Reissue of:
(64) Patent No.: 7,754,460
Issued: Jul. 13, 2010
Appl. No.: 11/595,537
Filed: Nov. 9, 2006

U.S. Applications:
(63) Continuation-in-part of application No. 10/581,014, filed as application No. PCT/US2004/040438 on Dec. 3, 2004.

(60) Provisional application No. 60/526,764, filed on Dec. 3, 2003.

(51) Int. Cl.

| | |
|---|---|
| ***C12N 9/14*** | (2006.01) |
| ***C12N 1/20*** | (2006.01) |
| ***C12P 21/06*** | (2006.01) |
| ***C11D 3/386*** | (2006.01) |
| ***C11D 3/00*** | (2006.01) |
| ***C07H 21/04*** | (2006.01) |

(52) U.S. Cl.
USPC .... 435/195; 435/69.1; 435/252.3; 435/320.1; 510/305; 510/320; 536/23.2

(58) Field of Classification Search
None
See application file for complete search history.

(56) References Cited

U.S. PATENT DOCUMENTS

| | | | |
|---|---|---|---|
| 3,974,082 | A | 8/1976 | Weyn |
| 4,261,868 | A | 4/1981 | Hora et al. |
| 4,400,237 | A | 8/1983 | Kruger et al. |
| 4,404,128 | A | 9/1983 | Anderson |
| 4,430,243 | A | 2/1984 | Bragg |
| 4,977,252 | A | 12/1990 | Chiu |
| 5,030,240 | A | 7/1991 | Wiersema et al. |
| 5,108,457 | A | 4/1992 | Poulouse et al. |
| 5,204,015 | A | 4/1993 | Caldwell et al. |
| 5,254,283 | A | 10/1993 | Arnold et al. |
| 5,296,616 | A | 3/1994 | Namekawa et al. |
| 5,352,594 | A | 10/1994 | Poulouse |
| 5,354,559 | A | 10/1994 | Morehouse |
| 5,370,770 | A | 12/1994 | Johnson et al. |
| 5,486,303 | A | 1/1996 | Capeci et al. |
| 5,489,392 | A | 2/1996 | Capeci et al. |
| 5,516,448 | A | 5/1996 | Capeci et al. |
| 5,565,422 | A | 10/1996 | Del Greco et al. |
| 5,569,645 | A | 10/1996 | Dinniwell et al. |
| 5,574,005 | A | 11/1996 | Welch et al. |
| 5,576,282 | A | 11/1996 | Miracle et al. |
| 5,595,967 | A | 1/1997 | Miracle et al. |
| 5,597,936 | A | 1/1997 | Perkins et al. |
| 5,601,750 | A | 2/1997 | Domke et al. |
| 5,691,297 | A | 11/1997 | Nassano et al. |
| 5,785,812 | A | 7/1998 | Linsten et al. |
| 5,879,584 | A | 3/1999 | Bianchetti et al. |
| 5,935,826 | A | 8/1999 | Blue et al. |
| 5,989,526 | A | 11/1999 | Aaslying et al. |
| 6,165,318 | A | 12/2000 | Paren et al. |
| 6,225,464 | B1 | 5/2001 | Hiler, II et al. |
| 6,306,812 | B1 | 10/2001 | Perkins et al. |
| 6,326,348 | B1 | 12/2001 | Vinson et al. |
| 6,379,653 | B1 | 4/2002 | Asyng et al. |
| 6,569,286 | B1 | 5/2003 | Withenshaw et al. |
| 2002/0007516 | A1 | 1/2002 | Wang |
| 2003/0191033 | A1 | 10/2003 | Ryu et al. |
| 2008/0145353 | A1 | 6/2008 | Amin |

FOREIGN PATENT DOCUMENTS

| | | | |
|---|---|---|---|
| EP | 0 248 660 | | 6/1987 |
| EP | 0248660 | | 12/1987 |
| EP | 0 922 499 | A2 | 10/1994 |
| EP | 0922499 | | 6/1999 |
| EP | 1 255 888 | | 2/2001 |
| EP | 1255888 | | 11/2002 |
| GB | 2 094 826 | A | 3/1982 |
| GB | 2094826 | | 3/1982 |
| WO | WO 97/11151 | | 9/1996 |
| WO | WO98/11151 | | 3/1998 |
| WO | WO 03/002810 | | 1/2003 |
| WO | WO 03/002810 | A1 | 1/2003 |
| WO | WO 2005/056782 | | 12/2004 |
| WO | WO 2005/056782 | | 6/2005 |
| WO | WO2007/067473 | | 7/2007 |

OTHER PUBLICATIONS

Altschul et al., "Basic Local Alignment Search Tool," J. Mol. Biol., V. 215, 1990, pp. 403-410.

Altschul et al., "Basic Local Alignment Statistics," Methods in Enzymology, V. 266, pp. 460-480 (1993).

Baldry, "The bactericidal, fungicidal and sporicidal properties of hydrogen peroxide and peracetic acid," J. of applied Bact., 1983, 54, 417-423.

Chang, Shing et al., "High Frequency Transformation of *Bacillus subtilis* Protoplasts by Plasmid DNA," Mol. Gen. Genet., 168:111-115, 1979.

(Continued)

*Primary Examiner* — Robert Mondesi
*Assistant Examiner* — Iqbal H Chowdhury
(74) *Attorney, Agent, or Firm* — Danisco US Inc.

(57) ABSTRACT

The present invention provides methods and compositions comprising at least one perhydrolase enzyme for cleaning and other applications. In some embodiments, the present invention provides methods and compositions for generation of long chain peracids. Certain embodiments of the present invention find particular use in applications involving cleaning, bleaching and disinfecting.

10 Claims, No Drawings

(56) References Cited

OTHER PUBLICATIONS

Devereux et al., "A Comprehensive set of sequence analysis programs for the VAX," Nucl. Acids Res., vol. 12, p. 387-395, 1984.
Feng et al., "Progressive Sequence Alignment as a Prerequisite to Correct Phylogenetic Tress" J. Mol Evol. vol. 25, pp. 351-360, 1987.
Ferrari, E. et al., in *Bacillus*, Harwood (ed.), Plenum Publishing Corporation, pp. 57-72, 1989.
Higgins et al., "Clustal: a package for performing multiple sequence alighment on a microcomputer," Gene, 73 (1988) 237-244.
Higgins et al., "Fast and sensitive multiple sequence alignments on microcomputer," CABIOS, vol. 5, 1989, p. 151-153.
Hofmann et al., "Bleaching Activators and the Mechanism of Bleaching Activation," J. prakt. Chem., 334 (1992) 293-297.
Karlin et al., "Applications and statistics for multiple high-scoring segments in molecular sequences," Proc. Natl. Acad. Sci. USA, vol. 90, pp. 5873-5877, Jun. 1993.
Karst should be Pinkemell et al., "Selective Phtometric Deermination of Peroxycarboxylic Acids in the Presence of Hydrogen Peroxide," Analyst, Jun. 1997, V. 122 567-571.
Mathews, I., et al. "Structure of a Novel Enzyme That Catalyzes Acyl Transfer to Alcohols in Aqueous Conditions," Biochemistry 2007, 46, 8969-8979.
Needleman et al., "A General Method Applicable to the Search for Similarities in the Amino Acid Sequence of Two Proteins," J. Mol. Biol., vol. 48, pp. 443-453, 1970.
Pearson et al., "Improved tools for biological sequence comparison," Proc. Natl. Acad. Sci. USA, vol. 85, pp. 2444-2448, Apr. 1988.
Smith et al., "Comparison of Biosequences," Adv. In Appl. Math. vol. 2, pp. 482-489, 1981.
Upton et al., "A New Family of Llpolytic enzymes?". TIBS, V. 20—pp. 178-179 May 1995.
Whisstock et al. "Prediction of Protein Function from Protein Sequence and Structure," *Quarterly Reviews of Biophysics* 36(3): 307-340, 2003.
Written Opinion of the International Searching Authority for PCT/US07/23327 dated May 9, 2009, 5 pp.
International Search Report for PCT/US07/23327 dated Apr. 16, 2008, 2 pp.
Whisstock et al. Quaterly Reviews of Biophysics, 2003, "Prediction of protein function from protein sequence and structure", 36(3): 307-340.*
Henikoff, Steven et al., "Amino acid substitution matrices from protein blocks," *Proc. Natl. Acad. Sci. USA*, 89:10915-10919, Nov. 1992.
Smith et al., "Comparison of Biosequences," Adv. In App. Math. vol. 2, pp. 482-489, 1981.
Smith, Michael et al., "Protoplast Transformation in Coryneform Bacteria and Introduction of an α-Amylase Gene from *Bacillus amyloliquefaciens* into *Brevibacterium lactofermenturn," Applied and Environmental Microbiology*, vol. 51, No. 3, pp. 634-639, Mar. 1986.

* cited by examiner

ENZYME FOR THE PRODUCTION OF LONG CHAIN PERACID

Matter enclosed in heavy brackets [ ] appears in the original patent but forms no part of this reissue specification; matter printed in italics indicates the additions made by reissue.

CROSS-REFERENCE

The present application is a Continuation-in-Part of pending U.S. patent application Ser. No. 10/581,014, filed on Sep. 11, 2007, which application is a U.S. National phase filing of International Patent Application Serial No. PCT/US04/040438 under 35 U.S.C. §371, which application claims the benefit of U.S. Provisional Patent Application Ser. No. 60/526,764, filed Dec. 3, 2003, now abandoned.

*SEQUENCE LISTING*

*The sequence listing submitted via EFS, in compliance with 37 C.F.R. §1.52(e), is incorporated herein by reference. The sequence listing text file submitted via EFS contains the file "30936USRE_SequenceListing", created on Aug. 9, 2012, which is 8,565 bytes in size.*

FIELD OF THE INVENTION

The present invention provides methods and compositions comprising at least one perhydrolase enzyme for cleaning and other applications. In some embodiments, the present invention provides methods and compositions for generation of long chain peracids. Certain embodiments of the present invention find particular use in applications involving cleaning, bleaching and disinfecting.

BACKGROUND

Detergent and other cleaning compositions typically include a complex combination of active ingredients. For example, most cleaning products include a surfactant system, enzymes for cleaning, bleaching agents, builders, suds suppressors, soil-suspending agents, soil-release agents, optical brighteners, softening agents, dispersants, dye transfer inhibition compounds, abrasives, bactericides, and perfumes. Despite the complexity of current detergents, there are many stains that are difficult to completely remove. Furthermore, there is often residue build-up, which results in discoloration (e.g., yellowing) and diminished aesthetics due to incomplete cleaning. These problems are compounded by the increased use of low (e.g., cold water) wash temperatures and shorter washing cycles. Moreover, many stains are composed of complex mixtures of fibrous material, mainly incorporating carbohydrates and carbohydrate derivatives, fiber, and cell wall components (e.g., plant material, wood, mud/clay based soil, and fruit). These stains present difficult challenges to the formulation and use of cleaning compositions.

In addition, colored garments tend to wear and show appearance losses. A portion of this color loss is due to abrasion in the laundering process, particularly in automated washing and drying machines. Moreover, tensile strength loss of fabric appears to be an unavoidable result of mechanical and chemical action due to use, wearing, and/or washing and drying. Thus, a means to efficiently and effectively wash colored garments so that these appearance losses are minimized is needed.

Cleaning compositions that comprise esterases, lipases and cutinases are well-known in the art. However, these enzymes have a very low ratio of perhydrolysis to hydrolysis. This results in the conversion of most of the ester substrate into acid, instead of the more desirable peracid. This is a serious drawback, since formula space and cost considerations render it feasible to include only a limited amount of substrate.

In sum, despite improvements in the capabilities of cleaning compositions, there remains a need in the art for detergents that remove stains, maintain fabric color and appearance, and prevent dye transfer. In addition, there remains a need for detergent and/or fabric care compositions that provide and/or restore tensile strength, as well as provide anti-wrinkle, anti-bobbling, and/or anti-shrinkage properties to fabrics, as well as provide static control, fabric softness, maintain the desired color appearance, and fabric anti-wear properties and benefits. In particular, there remains a need for the inclusion of compositions that are capable of removing the colored components of stains, which often remain attached to the fabric being laundered. In addition, there remains a need for improved methods and compositions suitable for textile bleaching.

In addition to the fabric and garment cleaning area, bleaching is commonly used in the pulp and paper industry. Prior to production of paper, pulp is typically treated to remove undesirable colored contaminants. This provides pulp that is suitable for production of paper of higher quality than pulp that is not treated to remove colored contaminants and other undesirable components present in pulp. For example, in the paper recycling industry, removal of ink is necessary. Although standard methods are suitable for deinking paper with oil or water-based inks, the increased use of electrostatic inks has made deinking problematic, as these inks are much more difficult to remove. There are various methods available for deinking paper, including the use of enzymes (See e.g., U.S. Pat. No. 5,370,770). However, there remains a need in the art for efficient, cost-effective methods for treatment of pulp for paper (recycled and new) product production.

Bleaching is also commonly used in the personal care market (e.g., dental whiteners, hair bleachers, etc.). Although personal care bleaching products have improved over the years, there remains a need for mild, easy to use, cost-effective bleaching methods for this setting.

SUMMARY OF THE INVENTION

The present invention provides methods and compositions comprising at least one perhydrolase enzyme for cleaning and other applications. In some embodiments, the present invention provides methods and compositions for generation of long chain peracids. Certain embodiments of the present invention find particular use in applications involving cleaning, bleaching and disinfecting.

The present invention provides an isolated perhydrolase enzyme that perhydrolyzes long chain acyl ester substrates. In some embodiments, the enzyme produces long chain peracid in the presence of a long chain acyl ester substrate and peroxide. In some preferred embodiments, the long chain acyl ester substrate contains a chain of at least six carbon atoms. In some particularly preferred embodiments, the long chain acyl ester substrate contains a chain of at least nine carbon atoms.

In certain embodiments, the subject perhydrolase enzyme has an amino acid sequence that is at least 80% identical to the amino acid sequence of a naturally-occurring perhydrolase (i.e., a wild-type perhydrolase encoded by a genome of a cell). In some embodiments, the enzyme has an amino acid sequence that is at least 80% identical to the naturally-occurring M. smegmatis perhydrolase (SEQ ID NO:2). In some embodiments, the perhydrolase enzyme comprises at least one substitution at an amino acid position equivalent to a position in M. smegmatis perhydrolase comprising the amino acid sequence set forth in SEQ ID NO:2, wherein said at least one substitution is selected from positions 12, 22, 59, 153, 154, 194, 196, and 204. In some particularly preferred embodiments, the enzyme has any one or combination of the following amino acids: a Gly, Pro or Gln at position 12, a Trp at position 22, a Pro at position 59, a Pro at position 153, a Thr, Ser, Val, or Gln at position 154, a Gly at position 194, a Ser, Gln, Val, Gly, Pro, Ile or His at position 196 or a Tyr or Trp at position 204, where the amino acid positions are positionally equivalent to positions 12, 22, 59, 153, 154, 194, 196 and 204 in the M. smegmatis perhydrolase of SEQ ID NO:2. In some other embodiments, the enzyme contains the following amino acids: an Ala at position 154 and a Met at position 194, a Gly at position 154 and a Val at position 194, or a Gly at position 12 and a Met at position 194, a Thr at position 154 and an Ile at position 196, a Gln at position 12 and a Val at position 154, a Met at position 12 and a Glu at position 154, A Gly at position 12 and a Gly at position 154, a Glu at position 154 and a Ser at position 194, or a Gly at position 12 and a Trp at position 22, or any combination thereof, where the amino acid positions are positionally equivalent to positions 12, 22, 59, 153, 154, 194, 196 and 204 of the M. smegmatis perhydrolase of SEQ ID NO:2. In some preferred embodiments, the perhydrolase enzyme of the present invention has a perhydrolysis:hydrolysis ratio of at least 1, and/or a low hydrolysis rate as compared with SEQ ID NO:2.

The present invention also provides isolated perhydrolase enzymes, wherein the enzyme hydrolyzes long chain acyl ester substrates. In some embodiments, the enzyme produces long chain peracid in the presence of a long chain acyl ester substrate and peroxide. In additional embodiments, the chain acyl ester substrate contains a chain of at least six carbon atoms. In yet further embodiments, the long chain acyl ester substrate contains a chain of at least nine carbon atoms.

The present invention also provides an isolated nucleic acid encoding the isolated perhydrolase enzymes of the present invention. In some preferred embodiments, the recombinant nucleic acid contains: a promoter and the isolated nucleic acid, wherein the promoter and isolated nucleic acid are operably linked to provide for transcription of the isolated nucleic acid.

The present invention also provides vectors comprising recombinant nucleic acid of the present invention. Host cells containing the vectors are also provided. If present in a host cell, the recombinant nucleic acid may present in the genome of the cell or in a vector that autonomously replicates in the cell. In particular embodiments, the recombinant nucleic acid provides for secretion of the isolated perhydrolase protein from the host cell. The host cell may be a bacterial or fungal host cell. A culture containing a subject host cell and culture medium is provided. The culture medium may contain perhydrolase protein secreted from the cell.

The present invention also provides methods for making the perhydrolase enzymes of the present invention. In general terms, the methods include cultivating the subject host cell under conditions suitable for the production of the perhydrolase. In some preferred embodiments, the perhydrolase is recovered from growth medium. In some particularly preferred embodiments, the recovered perhydrolase is combined with other reagents to produce a cleaning composition.

The present invention further provides cleaning compositions comprising at least one perhydrolase of the present invention. In some preferred embodiments, the cleaning composition further comprises a long chain acyl ester substrate and a source of peroxide, which, together with the perhydrolase enzyme produce long chain peracid. In certain embodiments, the cleaning composition furthers contain at least one surfactant. In some particular embodiments, the cleaning composition is a laundry detergent.

The cleaning compositions of the present invention find use in cleaning substrates (e.g., a fabric), by contacting the composition with the substrate.

DESCRIPTION OF THE INVENTION

The present invention provides methods and compositions comprising at least one perhydrolase enzyme for cleaning and other applications. In some embodiments, the present invention provides methods and compositions for generation of long chain peracids. Certain embodiments of the present invention find particular use in applications involving cleaning, bleaching and disinfecting.

Unless otherwise indicated, the practice of the present invention involves conventional techniques commonly used in molecular biology, microbiology, protein purification, protein engineering, protein and DNA sequencing, recombinant DNA, chemistry, biochemistry, and enzymology fields, which are within the skill of those in the art. Indeed, such techniques are known to those of skill in the art and are described in numerous texts and reference works (See e.g., Sambrook et al., "Molecular Cloning: A Laboratory Manual", 2nd Ed. (Cold Spring Harbor), [1989]); and Ausubel et al., "Current Protocols in Molecular Biology" [1987]). All patents, patent applications, articles and publications mentioned herein, both supra and infra, are hereby expressly incorporated herein by reference.

Furthermore, the headings provided herein are not limitations of the various aspects or embodiments of the invention which can be had by reference to the specification as a whole. Accordingly, the terms defined immediately below are more fully defined by reference to the specification as a whole. Nonetheless, in order to facilitate understanding of the invention, a number of terms are defined below.

DEFINITIONS

Unless defined otherwise herein, all technical and scientific terms used herein have the same meaning as commonly understood by one of ordinary skill in the art to which this invention pertains. For example, Singleton and Sainsbury, Dictionary of Microbiology and Molecular Biology, 2d Ed., John Wiley and Sons, NY (1994); and Hale and Marham, The Harper Collins Dictionary of Biology, Harper Perennial, N.Y. (1991) provide those of skill in the art with a general dictionaries of many of the terms used in the invention. Although any methods and materials similar or equivalent to those described herein find use in the practice of the present invention, the preferred methods and materials are described herein. Accordingly, the terms defined immediately below are more fully described by reference to the Specification as a whole. Also, as used herein, the singular terms "a," "an," and "the" include the plural reference unless the context clearly indicates otherwise. Unless otherwise indicated, nucleic acids are written left to right in 5' to 3' orientation; amino acid sequences are written left to right in amino to carboxy orientation, respectively. It is to be understood that this invention is not limited to the particular methodology, protocols, and reagents described, as these may vary, depending upon the context they are used by those of skill in the art.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

As used herein, a "peracid" is an acid of the formula RC(=O)OOH, where R is any organic moiety.

As used herein, a "long chain peracid" is a peracid of the formula RC(=O)OOH, where R is any organic moiety that contains a chain of 6 or more carbon atoms. Long chain peracids may contain a carbon chain of 6-10 carbon atoms (i.e., a $C_6$-$C_{10}$ carbon chain) or a carbon chain of at least 11 carbon atoms (i.e., a $C_{11+}$ carbon chain). Exemplary long chain peracids contain a $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$ or $C_{22}$ carbon chain. Exemplary long chain peracids include, but are not limited to percaproic acid, percaprylic acid, pernonanoic acid, perdecanoic acid, perdodecanoic acid, permyristic acid, perpalmitic acid, perstearic acid, and peroleic acid.

As used herein, the term "perhydrolyze" refers to an enzymatic reaction that produces a peracid. In some embodiments, a peracid is produced by perhydrolysis of an ester substrate of the formula $R_1C(=O)OR_2$, where $R_1$ and $R_2$ are independently any organic moiety, in the presence of hydrogen peroxide ($H_2O_2$).

As used herein, a "long chain acyl ester" is a ester of the formula $R_1C(=O)OR_2$, where $R_1$ is any organic moiety that contains a chain of at least 6 carbon atoms and $R_2$ is any organic moiety. Long chain acyl esters may contain a carbon chain of 6-10 carbon atoms (i.e., a $C_6$-$C_{10}$ carbon chain) or a carbon chain of at least 11 carbon atoms (i.e., a $C_{11+}$ carbon chain). Exemplary long chain acyl esters contain a $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$ or $C_{22}$ carbon chain. Exemplary long chain acyl esters include: caproic acid ester, caprylic acid ester, nonanoic acid ester, decanoic acid ester, dodecanoic acid ester, myristic acid ester, palmitic acid ester, stearic acid ester, and oleic acid ester.

As used herein, the term "source of hydrogen peroxide" includes hydrogen peroxide as well as the components of a system that can spontaneously or enzymatically produce hydrogen peroxide as a reaction product.

As used herein, the term "bleaching" refers to the treatment of a material (e.g., fabric, laundry, pulp, etc.) or any surface for a sufficient length of time and under appropriate pH and temperature conditions to effect a brightening (i.e., whitening) and/or cleaning of the material. Examples of chemicals suitable for bleaching include but are not limited to $ClO_2$, $H_2O_2$, peracids, $NO_2$, etc.

As used herein, the term "disinfecting" refers to the removal of contaminants from surfaces, as well as the inhibition or killing of microbes on the surfaces of items. It is not intended that the present invention be limited to any particular surface, item, or contaminant(s) or microbes to be removed.

As used herein, the term "perhydrolase" refers to an enzyme that is capable of catalyzing a reaction that results in the formation of sufficiently high amounts of peracid suitable for applications such as cleaning, bleaching, and disinfecting. In some preferred embodiments, the perhydrolase enzymes of the present invention perhydrolyze long chain acyl esters to produce long chain peracids, which are suitable for use in a wide variety of cleaning-related applications. In some particularly preferred embodiments, the perhydrolases of the present invention are characterized by having distinct tertiary structure and primary sequence. In some additional particularly preferred embodiments, perhydrolases of the present invention are variants of the M. smegmatis perhydrolase. However, it is not intended that the present invention be limited to these specific perhydrolases.

As used herein, the term "multimer" refers to two or more proteins or peptides that are covalently or non-covalently associated and exist as a complex in solution. A "dimer" is a multimer that contains two proteins or peptides; a "trimer" contains three proteins or peptides, etc. As used herein, "octamer" refers to a multimer of eight proteins or peptides.

As used herein, the phrase "perhydrolysis to hydrolysis ratio" refers to the ratio of the amount of enzymatically produced peracid to that of enzymatically produced acid by the perhydrolase, under defined conditions and within a defined time. In some embodiments, the assays provided herein are used to determine the amounts of peracid and acid produced by the enzyme.

As used herein, "personal care products" refers to products used in the cleaning, bleaching and/or disinfecting of hair, skin, scalp, and/or teeth, including, but not limited to shampoos, body lotions, shower gels, topical moisturizers, toothpaste, and/or other topical cleansers. In some particular embodiments, these products are utilized on humans, while in other embodiments, these products find use with non-human animals (e.g., in veterinary applications).

As used herein, "pharmaceutically-acceptable" refers to drugs, medicaments and/or inert ingredients which are suitable for use in contact with the tissues of humans and other animals without undue toxicity, incompatibility, instability, irritation, allergic response, and the like, commensurate with a reasonable benefit/risk ratio.

As used herein, "cleaning compositions" and "cleaning formulations" refer to compositions that find use in the removal of undesired compounds from items to be cleaned, such as fabrics, dishes, contact lenses, other solid substrates, hair (shampoos), skin (soaps and creams), teeth (mouthwashes, toothpastes) etc. The term encompasses any materials/compounds selected for the particular type of cleaning composition desired and the form of the product (e.g., liquid, gel, granule, or spray composition), as long as the composition is compatible with the perhydrolase and other enzyme(s) used in the composition. The specific selection of cleaning composition materials is readily made by considering the surface, item or fabric to be cleaned, and the desired form of the composition for the cleaning conditions during use.

The terms further refer to any composition that is suited for cleaning, bleaching, disinfecting, and/or sterilizing any object and/or surface. It is intended that the terms include, but are not limited to detergent compositions (e.g., liquid and/or solid laundry detergents, fine fabric detergents; hard surface cleaning formulations, such as for glass, wood, ceramic and metal counter tops and windows; carpet cleaners; oven cleaners; fabric fresheners; fabric softeners; and textile and laundry pre-spotters, as well as dish detergents).

Indeed, the term "cleaning composition" as used herein, includes, unless otherwise indicated, granular or powder-form all-purpose or heavy-duty washing agents, especially cleaning detergents; liquid, gel or paste-form all-purpose washing agents, especially the so-called heavy-duty liquid (HDL) types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, mouthwashes, denture cleaners, car or carpet shampoos, bathroom cleaners; hair shampoos and hair-rinses; shower gels and foam baths and metal cleaners; as well as cleaning auxiliaries such as bleach additives and "stain-stick" or pre-treat types.

As used herein, the terms "detergent composition" and "detergent formulation" are used in reference to mixtures which are intended for use in a wash medium for the cleaning of soiled objects. In particular embodiments, the term is used in reference to laundering fabrics and/or garments (e.g., "laundry detergents"). In alternative embodiments, the term refers to other detergents, such as those used to clean dishes, cutlery, etc. (e.g., "dishwashing detergents"). It is not intended that the present invention be limited to any particular detergent formulation or composition. Indeed, it is intended that in addition to perhydrolase, the term encompasses detergents that contain surfactants, transferase(s), hydrolytic enzymes, oxido reductases, builders, bleaching agents, bleach activators, bluing agents and fluorescent dyes, caking inhibitors, masking agents, enzyme activators, antioxidants, and solubilizers.

As used herein, "enhanced performance" in a detergent is defined as increasing cleaning of bleach-sensitive stains (e.g., grass, tea, wine, blood, dingy, etc.), as determined by usual evaluation after a standard wash cycle. In particular embodiments, the perhydrolase of the present invention provides enhanced performance in the oxidation and removal of colored stains and soils. In further embodiments, the perhydrolase of the present invention provides enhanced performance in the removal and/or decolorization of stains. In yet additional embodiments, the perhydrolase of the present invention provides enhanced performance in the removal of lipid-based stains and soils. In still further embodiments, the perhydrolase of the present invention provides enhanced performance in removing soils and stains from dishes and other items.

As used herein the term "hard surface cleaning composition," refers to detergent compositions for cleaning hard surfaces such as floors, walls, tile, bath and kitchen fixtures, and the like. Such compositions are provided in any form, including but not limited to solids, liquids, emulsions, etc.

As used herein, "dishwashing composition" refers to all forms for compositions for cleaning dishes, including but not limited to granular and liquid forms.

As used herein, "fabric cleaning composition" refers to all forms of detergent compositions for cleaning fabrics, including but not limited to, granular, liquid and bar forms.

As used herein, "textile" refers to woven fabrics, as well as staple fibers and filaments suitable for conversion to or use as yarns, woven, knit, and non-woven fabrics. The term encompasses yarns made from natural, as well as synthetic (e.g., manufactured) fibers.

As used herein, "textile materials" is a general term for fibers, yarn intermediates, yarn, fabrics, and products made from fabrics (e.g., garments and other articles).

As used herein, "fabric" encompasses any textile material. Thus, it is intended that the term encompass garments, as well as fabrics, yarns, fibers, non-woven materials, natural materials, synthetic materials, and any other textile material.

As used herein, the term "compatible," means that the cleaning composition materials do not reduce the enzymatic activity of the perhydrolase to such an extent that the perhydrolase is not effective as desired during normal use situations. Specific cleaning composition materials are exemplified in detail hereinafter.

As used herein, "effective amount of perhydrolase enzyme" refers to the quantity of perhydrolase enzyme necessary to achieve the enzymatic activity required in the specific application (e.g., personal care product, cleaning composition, etc.). Such effective amounts are readily ascertained by one of ordinary skill in the art and are based on many factors, such as the particular enzyme variant used, the cleaning application, the specific composition of the cleaning composition, and whether a liquid or dry (e.g., granular, bar) composition is required, and the like.

As used herein, "non-fabric cleaning compositions" encompass hard surface cleaning compositions, dishwashing compositions, personal care cleaning compositions (e.g., oral cleaning compositions, denture cleaning compositions, personal cleansing compositions, etc.), and compositions suitable for use in the pulp and paper industry.

As used herein, "oral cleaning compositions" refers to dentifrices, toothpastes, toothgels, toothpowders, mouthwashes, mouth sprays, mouth gels, chewing gums, lozenges, sachets, tablets, biogels, prophylaxis pastes, dental treatment solutions, and the like. Oral care compositions that find use in conjunction with the perhydrolases of the present invention are well known in the art (See e.g., U.S. Pat. Nos. 5,601,750, 6,379,653, and 5,989,526, all of which are incorporated herein by reference).

As used herein, "pulp treatment compositions" refers to the use of the present perhydrolase enzymes in compositions suitable for use in papermaking. It is intended that the term encompass compositions suitable for the treatment of any pulp material, including wood, as well as non-wood materials, such as "agricultural residues" and "fiber crops," including but not limited to wheat straw, rice straw, corn stalks, bagasse (sugar cane), rye grass straw, seed flax straw, flax straw, kenaf, industrial hemp, sisal, textile flat straw, hesperaloe, etc. Thus, the present invention also encompasses the use of the perhydrolases of the present invention in pulp treatment methods.

As used herein, "oxidizing chemical" refers to a chemical that has the capability of bleaching pulp or any other material. The oxidizing chemical is present at an amount, pH and temperature suitable for bleaching. The term includes, but is not limited to hydrogen peroxide and peracids.

As used herein, "acyl" is the general name for organic acid groups, which are the residues of carboxylic acids after removal of the —OH group (e.g., ethanoyl chloride, $CH_3CO—Cl$, is the acyl chloride formed from ethanoic acid, $CH_3COO—H$). The names of the individual acyl groups are formed by replacing the "-ic" of the acid by "-yl."

As used herein, the term "acylation" refers to the chemical transformation which substitutes the acyl (RCO—) group into a molecule, generally for an active hydrogen of an —OH group.

As used herein, the term "transferase" refers to an enzyme that catalyzes the transfer of functional compounds to a range of substrates.

As used herein, "leaving group" refers to the nucleophile which is cleaved from the acyl donor upon substitution by another nucleophile.

As used herein, the term "enzymatic conversion" refers to the modification of a substrate to an intermediate or the modification of an intermediate to an end-product by contacting the substrate or intermediate with an enzyme. In some embodiments, contact is made by directly exposing the substrate or intermediate to the appropriate enzyme. In other embodiments, contacting comprises exposing the substrate or intermediate to an organism that expresses and/or excretes the enzyme, and/or metabolizes the desired substrate and/or intermediate to the desired intermediate and/or end-product, respectively.

As used herein, the phrase "detergent stability" refers to the stability of a detergent composition. In some embodiments, the stability is assessed during the use of the detergent, while in other embodiments, the term refers to the stability of a detergent composition during storage.

As used herein, the phrase, "stability to proteolysis" refers to the ability of a protein (e.g., an enzyme) to withstand proteolysis. It is not intended that the term be limited to the use of any particular protease to assess the stability of a protein.

As used herein, "oxidative stability" refers to the ability of a protein to function under oxidative conditions. In particular, the term refers to the ability of a protein to function in the presence of various concentrations of $H_2O_2$ and/or peracid. Stability under various oxidative conditions can be measured either by standard procedures known to those in the art and/or by the methods described herein. A substantial change in oxidative stability is evidenced by at least about a 5% or greater increase or decrease (in most embodiments, it is preferably an increase) in the half-life of the enzymatic activity, as compared to the enzymatic activity present in the absence of oxidative compounds.

As used herein, "pH stability" refers to the ability of a protein to function at a particular pH. In general, most enzymes have a finite pH range at which they will function. In addition to enzymes that function in mid-range pHs (i.e., around pH 7), there are enzymes that are capable of working under conditions with very high or very low pHs. Stability at various pHs can be measured either by standard procedures known to those in the art and/or by the methods described herein. A substantial change in pH stability is evidenced by at least about 5% or greater increase or decrease (in most embodiments, it is preferably an increase) in the half-life of the enzymatic activity, as compared to the enzymatic activity at the enzyme's optimum pH. However, it is not intended that the present invention be limited to any pH stability level nor pH range.

As used herein, "thermal stability" refers to the ability of a protein to function at a particular temperature. In general, most enzymes have a finite range of temperatures at which they will function. In addition to enzymes that work in mid-range temperatures (e.g., room temperature), there are enzymes that are capable of working in very high or very low temperatures. Thermal stability can be measured either by known procedures or by the methods described herein. A substantial change in thermal stability is evidenced by at least about 5% or greater increase or decrease (in most embodiments, it is preferably an increase) in the half-life of the catalytic activity of a mutant when exposed to a different temperature (i.e., higher or lower) than optimum temperature for enzymatic activity. However, it is not intended that the present invention be limited to any temperature stability level nor temperature range.

As used herein, the term "chemical stability" refers to the stability of a protein (e.g., an enzyme) towards chemicals that adversely affect its activity. In some embodiments, such chemicals include, but are not limited to hydrogen peroxide, peracids, anionic detergents, cationic detergents, non-ionic detergents, chelants, etc. However, it is not intended that the present invention be limited to any particular chemical stability level nor range of chemical stability.

As used herein, the phrase "perhydrolase activity improvement" refers to the relative improvement of perhydrolase activity, in comparison with a standard enzyme. In some embodiments, the term refers to an improved rate of perhydrolysis product, while in other embodiments, the term encompasses perhydrolase compositions that produce less hydrolysis product. In additional embodiments, the term refers to perhydrolase compositions with altered substrate specificity.

As used herein, the phrase "alteration in substrate specificity" refers to changes in the substrate specificity of an enzyme. In some embodiments, a change in substrate specificity is defined as a difference between the $K_{cat}/K_m$ ratio observed with an enzyme compared to enzyme variants or other enzyme compositions. Enzyme substrate specificities vary, depending upon the substrate tested. The substrate specificity of an enzyme is determined by comparing the catalytic efficiencies it exhibits with different substrates. These determinations find particular use in assessing the efficiency of mutant enzymes, as it is generally desired to produce variant enzymes that exhibit greater ratios for particular substrates of interest. For example, the perhydrolase enzymes of the present invention are more efficient in producing peracid from an ester substrate than enzymes currently being used in cleaning, bleaching and disinfecting applications. Another example of the present invention is a perhydrolase with a lower activity on peracid degradation compared to the wild type. Another example of the present invention is a perhydrolase with higher activity on more hydrophobic acyl groups than acetic acid. However, it is not intended that the present invention be limited to any particular substrate composition nor any specific substrate specificity.

As used herein, "surface property" is used in reference to an electrostatic charge, as well as properties such as the hydrophobicity and/or hydrophilicity exhibited by the surface of a protein.

As used herein, the phrase "is independently selected from the group consisting of . . . " means that moieties or elements that are selected from the referenced Markush group can be the same, can be different or any mixture of elements as indicated in the following example:

A molecule having 3 R groups wherein each R group is independently selected from the group consisting of A, B and C. Here the three R groups may be: AAA, BBB, CCC, AAB, AAC, BBA, BBC, CCA, CCB, or ABC.

In reference to chemical compositions, the term "substituted" as used herein, means that the organic composition or radical to which the term is applied is:

(a) made unsaturated by the elimination of at least one element or radical; or (b) at least one hydrogen in the compound or radical is replaced with a moiety containing one or more (i) carbon, (ii) oxygen, (iii) sulfur, (iv) nitrogen or (v) halogen atoms; or (c) both (a) and (b).

Moieties which may replace hydrogen as described in (b) immediately above, that contain only carbon and hydrogen atoms, are hydrocarbon moieties including, but not limited to alkyl, alkenyl, alkynyl, alkyldienyl, cycloalkyl, phenyl, alkyl phenyl, naphthyl, anthryl, phenanthryl, fluoryl, steroid groups, and combinations of these groups with each other and with polyvalent hydrocarbon groups such as alkylene, alkylidene and alkylidyne groups. Moieties containing oxygen atoms that may replace hydrogen as described in (b) immediately above include, but are not limited to, hydroxy, acyl or keto, ether, epoxy, carboxy, and ester containing groups. Moieties containing sulfur atoms that may replace hydrogen as described in (b) immediately above include, but are not limited to, the sulfur-containing acids and acid ester groups, thioether groups, mercapto groups and thioketo groups. Moieties containing nitrogen atoms that may replace hydrogen as described in (b) immediately above include, but are not limited to, amino groups, the nitro group, azo groups, ammonium groups, amide groups, azido groups, isocyanate groups, cyano groups and nitrile groups. Moieties containing halogen atoms that may replace hydrogen as described in (b) immediately above include chloro, bromo, fluoro, iodo groups and any of the moieties previously described where a hydrogen or a pendant alkyl group is substituted by a halo group to form a stable substituted moiety.

It is understood that any of the above moieties (b)(i) through (b)(v) can be substituted into each other in either a monovalent substitution or by loss of hydrogen in a polyvalent substitution to form another monovalent moiety that can replace hydrogen in the organic compound or radical.

As used herein, the terms "purified" and "isolated" refer to the removal of contaminants from a sample. For example, perhydrolases are purified by removal of contaminating proteins and other compounds within a solution or preparation that are not perhydrolases. In some embodiments, recombinant perhydrolases are expressed in bacterial or fungal host cells and these recombinant perhydrolases are purified by the removal of other host cell constituents; the percent of recombinant perhydrolase polypeptides is thereby increased in the sample.

As used herein, "protein of interest," refers to a protein (e.g., an enzyme or "enzyme of interest") which is being analyzed, identified and/or modified. Naturally-occurring, as well as recombinant proteins find use in the present invention.

As used herein, "protein" refers to any composition comprised of amino acids and recognized as a protein by those of skill in the art. The terms "protein," "peptide" and polypeptide are used interchangeably herein. Wherein a peptide is a portion of a protein, those skilled in the art understand the use of the term in context.

As used herein, functionally and/or structurally similar proteins are considered to be "related proteins." In some embodiments, these proteins are derived from a different genus and/or species, including differences between classes of organisms (e.g., a bacterial protein and a fungal protein). In some embodiments, these proteins are derived from a different genus and/or species, including differences between classes of organisms (e.g., a bacterial enzyme and a fungal enzyme). In additional embodiments, related proteins are provided from the same species. Indeed, it is not intended that the present invention be limited to related proteins from any particular source(s). In addition, the term "related proteins" encompasses tertiary structural homologs and primary sequence homologs (e.g., the perhydrolase of the present invention). In further embodiments, the term encompasses proteins that are immunologically cross-reactive. In some most particularly preferred embodiments, the related proteins of the present invention exhibit very high ratios of perhydrolysis to hydrolysis.

As used herein, the term "derivative" refers to a protein which is derived from a protein by addition of one or more amino acids to either or both the C- and N-terminal end(s), substitution of one or more amino acids at one or a number of different sites in the amino acid sequence, and/or deletion of one or more amino acids at either or both ends of the protein or at one or more sites in the amino acid sequence, and/or insertion of one or more amino acids at one or more sites in the amino acid sequence. The preparation of a protein derivative is preferably achieved by modifying a DNA sequence which encodes for the native protein, transformation of that DNA sequence into a suitable host, and expression of the modified DNA sequence to form the derivative protein.

Related (and derivative) proteins comprise "variant proteins." In some preferred embodiments, variant proteins differ from a parent protein and one another by a small number of amino acid residues. The number of differing amino acid residues may be one or more, preferably about 1, 2, 3, 4, 5, 10, 15, 20, 30, 40, 50, or more amino acid residues. In some preferred embodiments, the number of different amino acids between variants is between 1 and 10. In some particularly preferred embodiments, related proteins and particularly variant proteins comprise at least about 35%, about 40%, about 45%, about 50%, about 55%, about 60%, about 65%, about 70%, about 75%, about 80%, about 85%, about 90%, about 95%, about 97%, about 98%, or about 99% amino acid sequence identity. Additionally, a related protein or a variant protein as used herein, refers to a protein that differs from another related protein or a parent protein in the number of prominent regions. For example, in some embodiments, variant proteins have about 1, 2, 3, 4, 5, or 10 corresponding prominent regions that differ from the parent protein.

Several methods are known in the art that are suitable for generating variants of the perhydrolase enzymes of the present invention, including but not limited to site-saturation mutagenesis, scanning mutagenesis, insertional mutagenesis, random mutagenesis, site-directed mutagenesis, and directed-evolution, as well as various other recombinatorial approaches.

In certain embodiments, homologous proteins are engineered to produce enzymes with the desired activity(ies). In some particularly preferred embodiments, the engineered proteins are included within the SGNH-hydrolase family of proteins. In some embodiments, the engineered proteins comprise at least one or a combination of the following conserved residues: L6, W14, W34, L38, R56, D62, L74, L78, H81, P83, M90, K97, G110, L114, L135, F180, G205. In alternative embodiments, these engineered proteins comprise the GDSL (SEQ ID NO:28) and GRTT (SEQ ID NO:29) and/or ARTT (SEQ ID NO:30) motifs. In some further embodiments, the enzymes are multimers, including but not limited to dimers, octamers, and tetramers. In additional embodiments, the engineered proteins exhibit a perhydrolysis to hydrolysis ratio that is greater than 1.

An amino acid residue of a perhydrolase is equivalent to a residue of M. smegmatis perhydrolase if it is either homologous (i.e., having a corresponding position in either the primary and/or tertiary structure) or analogous to a specific residue or portion of that residue in M. smegmatis perhydrolase (i.e., having the same or similar functional capacity to combine, react, and/or chemically interact).

In some embodiments, in order to establish homology to primary structure, the amino acid sequence of a perhydrolase is directly compared to the M. smegmatis perhydrolase primary sequence and particularly to a set of residues known to be invariant in all perhydrolases for which sequence is known. After aligning the conserved residues, allowing for necessary insertions and deletions in order to maintain alignment (i.e., avoiding the elimination of conserved residues through arbitrary deletion and insertion), the residues equivalent to particular amino acids in the primary sequence of M. smegmatis perhydrolase are defined. In certain embodiments, alignment of conserved residues define 100% of the equivalent residues. However, alignment of greater than about 75% or as little as about 50% of conserved residues are also adequate to define equivalent residues. In preferred embodiments, conservation of the catalytic serine and histidine residues are maintained.

Conserved residues are used to define the corresponding equivalent amino acid residues of M. smegmatis perhydrolase in other perhydrolases (e.g., perhydrolases from other Mycobacterium species, as well as any other organisms).

In some embodiments of the present invention, the DNA sequence encoding M. smegmatis perhydrolase is modified. In some embodiments, the following residues are modified: Cys7, Asp10, Ser11, Leu12, Thr13, Trp14, Trp16, Pro24, Thr25, Leu53, Ser54, Ala55, Thr64, Asp65, Arg67, Cys77, Thr91, Asn94, Asp95, Tyr99, Val125, Pro138, Leu140, Pro146, Pro148, Trp149, Phe150, Ile153, Phe154, Thr159, Thr186, Ile192, Ile194, and Phe196. However, it is not intended that the present invention be limited to sequence that are modified at these positions. Indeed, it is intended that the present invention encompass various modifications and combinations of modifications.

In additional embodiments, equivalent residues are defined by determining homology at the level of tertiary and quarternary structure for a perhydrolase whose tertiary and quarternary structure has been determined by x-ray crystallography. In this context, "equivalent residues" are defined as those for which the atomic coordinates of two or more of the main chain atoms of a particular amino acid residue of the carbonyl hydrolase and M. smegmatis perhydrolase (N on N, CA on CA, C on C, and O on O) are within 0.13 nm and preferably 0.1 nm after alignment. Alignment is achieved after the best model has been oriented and positioned to give the maximum overlap of atomic coordinates of non-hydrogen protein atoms of the perhydrolase in question to the M. smegmatis perhydrolase. As known in the art, the best model is the crystallographic model giving the lowest R factor for experimental diffraction data at the highest resolution available. Equivalent residues which are functionally and/or structurally analogous to a specific residue of M. smegmatis perhydrolase are defined as those amino acids of the perhydrolases that preferentially adopt a conformation such that they either alter, modify or modulate the protein structure, to effect changes in substrate binding and/or catalysis in a manner defined and attributed to a specific residue of the M. smegmatis perhydrolase. Further, they are those residues of the perhydrolase (in cases where a tertiary structure has been obtained by x-ray crystallography), which occupy an analogous position to the extent that although the main chain atoms of the given residue may not satisfy the criteria of equivalence on the basis of occupying a homologous position, the atomic coordinates of at least two of the side chain atoms of the residue lie with 0.13 nm of the corresponding side chain atoms of M. smegmatis perhydrolase. The coordinates of the three dimensional structure of M. smegmatis perhydrolase were determined and are set forth in Example 14 of WO05/056782 and find use as outlined above to determine equivalent residues on the level of tertiary structure.

In some embodiments, some of the residues identified for substitution, insertion or deletion are conserved residues whereas others are not. The perhydrolase mutants of the present invention include various mutants, including those encoded by nucleic acid that comprises a signal sequence. In some embodiments of perhydrolase mutants that are encoded by such a sequence are secreted by an expression host. In some additional embodiments of perhydrolase mutants that are encoded by such a sequence are produced cytoplasmically by an expression host. In some further embodiments, the nucleic acid sequence comprises a homolog having a secretion signal.

Characterization of wild-type and mutant proteins is accomplished via any means suitable and is preferably based on the assessment of properties of interest. For example, pH and/or temperature, as well as detergent and/or oxidative stability is/are determined in some embodiments of the present invention. Indeed, it is contemplated that enzymes having various degrees of stability in one or more of these characteristics (e.g., pH, temperature, proteolytic stability, detergent stability, and/or oxidative stability) will find use. In still other embodiments, perhydrolases with low peracid degradation activity are selected. In yet additional embodiments, perhydrolases with higher peracid formation are selected.

As used herein, "expression vector" refers to a DNA construct containing a DNA sequence that is operably linked to a suitable control sequence capable of effecting the expression of the DNA in a suitable host. Such control sequences include a promoter to effect transcription, an optional operator sequence to control such transcription, a sequence encoding suitable mRNA ribosome binding sites and sequences which control termination of transcription and translation. The vector may be a plasmid, a phage particle, or simply a potential genomic insert. Once transformed into a suitable host, the vector may replicate and function independently of the host genome, or may, in some instances, integrate into the genome itself. As used herein, "plasmid," "expression plasmid," and "vector" are often used interchangeably as the plasmid is the most commonly used form of vector at present. However, the invention is intended to include such other forms of expression vectors that serve equivalent functions and which are, or become, known in the art.

In some preferred embodiments, the perhydrolase gene is ligated into an appropriate expression plasmid. The cloned perhydrolase gene is then used to transform or transfect a host cell in order to express the perhydrolase gene. In some embodiments, this plasmid replicates in hosts in the sense that it contains the well-known elements necessary for plasmid replication, while in other embodiments, the plasmid is designed to integrate into the host chromosome. The necessary elements are provided for efficient gene expression (e.g., a promoter operably linked to the gene of interest). In some embodiments, these necessary elements are supplied as the gene's own homologous promoter if it is recognized, (i.e., transcribed by the host), a transcription terminator (e.g., a polyadenylation region for eukaryotic host cells) which is exogenous or is supplied by the endogenous terminator region of the perhydrolase gene. In some embodiments, a selection gene such as an antimicrobial resistance gene that enables continuous cultural maintenance of plasmid-infected host cells by growth in antimicrobial-containing media is also provided.

In some embodiments, the following cassette mutagenesis method finds use in facilitating the construction of the perhydrolase variants of the present invention, although other methods also find use in the present invention.

First, as described herein, a naturally-occurring gene encoding the perhydrolase is obtained and sequenced in whole or in part. Then, the sequence is scanned for a point at which it is desired to make a mutation (e.g., one or more deletion(s), insertion(s) and/or substitution(s)) of one or more amino acids in the encoded perhydrolase. The sequences flanking this point are evaluated for the presence of restriction sites for replacing a short segment of the gene with an oligonucleotide pool which when expressed will encode various mutants. Such restriction sites are preferably unique sites within the protein gene so as to facilitate the replacement of the gene segment. However, any convenient restriction site which is not overly redundant in the perhydrolase gene finds use in some embodiments, provided that the gene fragments generated by restriction digestion can be reassembled in proper sequence. If restriction sites are not present at locations within a convenient distance from the selected point (e.g., from 10 to 15 nucleotides), such sites are generated by substituting nucleotides in the gene in such a fashion that neither the reading frame nor the amino acids encoded are changed in the final construction. In some embodiments, mutation of the gene in order to change its sequence to conform to the desired sequence is accomplished by M13 primer extension in accord with generally known methods. The task of locating suitable flanking regions and evaluating the needed changes to arrive at two convenient restriction site sequences is made routine by the redundancy of the genetic code, a restriction enzyme map of the gene and the large number of different restriction enzymes. Note that if a convenient flanking restriction site is available, the above method need be used only in connection with the flanking region which does not contain a site.

Once the naturally-occurring DNA and/or synthetic DNA is cloned, the restriction sites flanking the positions to be mutated are digested with the cognate restriction enzymes and a plurality of end termini-complementary oligonucleotide cassettes are ligated into the gene. The mutagenesis is simplified by this method because all of the oligonucleotides can be synthesized so as to have the same restriction sites, and no synthetic linkers are necessary to create the restriction sites.

As used herein, "corresponding to," refers to a residue at the enumerated position in a protein or peptide, or a residue that is analogous, homologous, or equivalent to an enumerated residue in a protein or peptide.

As used herein, "corresponding region," generally refers to an analogous position along related proteins or a parent protein.

The terms "nucleic acid molecule encoding," "nucleic acid sequence encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the term "analogous sequence" refers to a sequence within a protein that provides similar function, tertiary structure, and/or conserved residues as the protein of interest (i.e., typically the original protein of interest). For example, in epitope regions that contain an alpha helix or a beta sheet structure, the replacement amino acids in the analogous sequence preferably maintain the same specific structure. The term also refers to nucleotide sequences, as well as amino acid sequences. In some embodiments, analogous sequences are developed such that the replacement amino acids result in a variant enzyme showing a similar or improved function. In some preferred embodiments, the tertiary structure and/or conserved residues of the amino acids in the protein of interest are located at or near the segment or fragment of interest. Thus, where the segment or fragment of interest contains, for example, an alpha-helix or a beta-sheet structure, the replacement amino acids preferably maintain that specific structure.

As used herein, "homologous protein" refers to a protein (e.g., perhydrolase) that has similar action and/or structure, as a protein of interest (e.g., an perhydrolase from another source). It is not intended that homologs be necessarily related evolutionarily. Thus, it is intended that the term encompass the same or similar enzyme(s) (i.e., in terms of structure and function) obtained from different species. In some preferred embodiments, it is desirable to identify a homolog that has a quaternary, tertiary and/or primary structure similar to the protein of interest, as replacement for the segment or fragment in the protein of interest with an analogous segment from the homolog will reduce the disruptiveness of the change. In some embodiments, homologous proteins induce similar immunological response(s) as a protein of interest.

As used herein, "homologous genes" refers to at least a pair of genes from different species, which genes correspond to each other and which are identical or very similar to each other. The term encompasses genes that are separated by speciation (i.e., the development of new species) (e.g., orthologous genes), as well as genes that have been separated by genetic duplication (e.g., paralogous genes). These genes encode "homologous proteins."

As used herein, "wild-type," "native," and "naturally-occurring" proteins are those found in nature. The terms "wild-type sequence," and "wild-type gene" are used interchangeably herein, to refer to a sequence that is native or naturally occurring in a host cell. In some embodiments, the wild-type sequence refers to a sequence of interest that is the starting point of a protein engineering project. The genes encoding the naturally-occurring protein may be obtained in accord with the general methods known to those skilled in the art. The methods generally comprise synthesizing labeled probes having putative sequences encoding regions of the protein of interest, preparing genomic libraries from organisms expressing the protein, and screening the libraries for the gene of interest by hybridization to the probes. Positively hybridizing clones are then mapped and sequenced.

The term "recombinant DNA molecule" as used herein refers to a DNA molecule that is comprised of segments of DNA joined together by means of molecular biological techniques.

The term "recombinant oligonucleotide" refers to an oligonucleotide created using molecular biological manipulations, including but not limited to, the ligation of two or more oligonucleotide sequences generated by restriction enzyme digestion of a polynucleotide sequence, the synthesis of oligonucleotides (e.g., the synthesis of primers or oligonucleotides) and the like.

The degree of homology between sequences may be determined using any suitable method known in the art (See e.g., Smith and Waterman, Adv. Appl. Math., 2:482 [1981]; Needleman and Wunsch, J. Mol. Biol., 48:443 [1970]; Pearson and Lipman, Proc. Natl. Acad. Sci. USA 85:2444 [1988]; programs such as GAP, BESTFIT, FASTA, and TFASTA in the Wisconsin Genetics Software Package (Genetics Computer Group, Madison, Wis.); and Devereux et al., Nucl. Acid Res., 12:387-395 [1984]).

For example, PILEUP is a useful program to determine sequence homology levels. PILEUP creates a multiple sequence alignment from a group of related sequences using progressive, pairwise alignments. It can also plot a tree showing the clustering relationships used to create the alignment. PILEUP uses a simplification of the progressive alignment method of Feng and Doolittle, (Feng and Doolittle, J. Mol. Evol., 35:351-360 [1987]). The method is similar to that described by Higgins and Sharp (Higgins and Sharp, CABIOS 5:151-153 [1989]). Useful PILEUP parameters including a default gap weight of 3.00, a default gap length weight of 0.10, and weighted end gaps. Another example of a useful algorithm is the BLAST algorithm, described by Altschul et al., (Altschul et al., J. Mol. Biol., 215:403-410, [1990]; and Karlin et al., Proc. Natl. Acad. Sci. USA 90:5873-5787 [1993]). One particularly useful BLAST program is the WU-BLAST-2 program (See, Altschul et al., Meth. Enzymol., 266:460-480 [1996]). parameters "W," "T," and "X" determine the sensitivity and speed of the alignment The BLAST program uses as defaults a wordlength (W) of 11, the BLOSUM62 scoring matrix (See, Henikoff and Henikoff, Proc.

Natl. Acad. Sci. USA 89:10915 [1989]) alignments (B) of 50, expectation (E) of 10, M'5, N'-4, and a comparison of both strands.

As used herein, "percent (%) nucleic acid sequence identity" is defined as the percentage of nucleotide residues in a candidate sequence that are identical with the nucleotide residues of the sequence.

As used herein, the term "hybridization" refers to the process by which a strand of nucleic acid joins with a complementary strand through base pairing, as known in the art.

As used herein, the phrase "hybridization conditions" refers to the conditions under which hybridization reactions are conducted. These conditions are typically classified by degree of "stringency" of the conditions under which hybridization is measured. The degree of stringency can be based, for example, on the melting temperature (Tm) of the nucleic acid binding complex or probe. For example, "maximum stringency" typically occurs at about Tm-5° C. (5° below the Tm of the probe); "high stringency" at about 5-10° below the Tm; "intermediate stringency" at about 10-20° below the Tm of the probe; and "low stringency" at about 20-25° below the Tm. Alternatively, or in addition, hybridization conditions can be based upon the salt or ionic strength conditions of hybridization and/or one or more stringency washes. For example, 6×SSC=very low stringency; 3×SSC=low to medium stringency; 1×SSC=medium stringency; and 0.5× SSC=high stringency. Functionally, maximum stringency conditions may be used to identify nucleic acid sequences having strict identity or near-strict identity with the hybridization probe, while high stringency conditions are used to identify nucleic acid sequences having about 80% or more sequence identity with the probe.

For applications requiring high selectivity, it is may be desirable to use relatively stringent conditions to form the hybrids (e.g., relatively low salt and/or high temperature conditions are used).

The phrases "substantially similar" and "substantially identical" in the context of at least two nucleic acids or polypeptides typically means that a polynucleotide or polypeptide comprises a sequence that has at least about 40% identity, more preferable at least about 50% identity, yet more preferably at least about 60% identity, preferably at least about 75% identity, more preferably at least about 80% identity, yet more preferably at least about 90%, still more preferably about 95%, most preferably about 97% identity, sometimes as much as about 98% and about 99% sequence identity, compared to the reference (e.g., wild-type) sequence. Sequence identity may be determined using known programs such as BLAST, ALIGN, and CLUSTAL using standard parameters. (See e.g., Altschul, et al., J. Mol. Biol. 215:403-410 [1990]; Henikoff et al., Proc. Natl. Acad. Sci. USA 89:10915 [1989]; Karin et al., Proc. Natl. Acad. Sci. USA 90:5873 [1993]; and Higgins et al., Gene 73:237-244 [1988]). Software for performing BLAST analyses is publicly available through the National Center for Biotechnology Information. Also, databases may be searched using FASTA (Pearson et al., Proc. Natl. Acad. Sci. USA 85:2444-2448 [1988]). One indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative substitution. Another indication that two nucleic acid sequences are substantially identical is that the two molecules hybridize to each other under stringent conditions (e.g., within a range of medium to high stringency).

As used herein, the terms "hybrid perhydrolases" and "fusion perhydrolases" refer to proteins that are engineered from at least two different or "parental" proteins. In preferred embodiments, these parental proteins are homologs of one another. For example, in some embodiments, a preferred hybrid perhydrolase or fusion protein contains the N-terminus of a protein and the C-terminus of a homolog of the protein. In some embodiments, the two terminal ends are combined to correspond to the full-length active protein.

The term "regulatory element" as used herein refers to a genetic element that controls some aspect of the expression of nucleic acid sequences. For example, a promoter is a regulatory element which facilitates the initiation of transcription of an operably linked coding region. Additional regulatory elements include splicing signals, polyadenylation signals and termination signals.

As used herein, "host cells" are generally prokaryotic or eukaryotic hosts which are transformed or transfected with vectors constructed using recombinant DNA techniques known in the art. Transformed host cells are capable of either replicating vectors encoding the protein variants or expressing the desired protein variant. In the case of vectors which encode the pre- or prepro-form of the protein variant, such variants, when expressed, are typically secreted from the host cell into the host cell medium.

The term "introduced" in the context of inserting a nucleic acid sequence into a cell, refers to methods such as transformation, transduction and transfection. Means of transformation include protoplast transformation, calcium chloride precipitation, electroporation, naked DNA, etc., as known in the art. (See, Chang and Cohen, Mol. Gen. Genet., 168:111-115 [1979]; Smith et al., Appl. Env. Microbiol., 51:634 [1986]; and the review article by Ferrari et al., in Harwood, Bacillius, Plenum Publishing Corp., pp. 57-72 [1989]).

As used herein, the term "promoter/enhancer" denotes a segment of DNA which contains sequences capable of providing both promoter and enhancer functions (for example, the long terminal repeats of retroviruses contain both promoter and enhancer functions). The enhancer/promoter may be "endogenous" or "exogenous" or "heterologous." An endogenous enhancer/promoter is one which is naturally linked with a given gene in the genome. An exogenous (heterologous) enhancer/promoter is one which is placed in juxtaposition to a gene by means of genetic manipulation (i.e., molecular biological techniques).

The presence of "splicing signals" on an expression vector often results in higher levels of expression of the recombinant transcript. Splicing signals mediate the removal of introns from the primary RNA transcript and consist of a splice donor and acceptor site (See e.g., Sambrook et al., Molecular Cloning: A Laboratory Manual, 2nd ed., Cold Spring Harbor Laboratory Press, New York [1989], pp. 16.7-16.8). A commonly used splice donor and acceptor site is the splice junction from the 16S RNA of SV40.

The term "stable transfection" or "stably transfected" refers to the introduction and integration of foreign DNA into the genome of the transfected cell. The term "stable transfectant" refers to a cell which has stably integrated foreign or exogenous DNA into the genomic DNA of the transfected cell.

The terms "selectable marker" or "selectable gene product" as used herein refer to the use of a gene which encodes an enzymatic activity that confers resistance to an antibiotic or drug upon the cell in which the selectable marker is expressed.

DETAILED DESCRIPTION OF THE INVENTION

The present invention provides methods and compositions comprising at least one perhydrolase enzyme for cleaning and other applications. In some embodiments, the present invention provides methods and compositions for generation of long chain peracids. Certain embodiments of the present invention find particular use in applications involving cleaning, bleaching and disinfecting.

In some embodiments, the present invention provides a perhydrolase enzyme that finds use in enzymatically generating long chain peracid from an ester substrate and hydrogen peroxide. The peracid produced by the subject perhydrolase depends on the ester substrate perhydrolyzed by the subject perhydrolase. In some embodiments, the peracid produced by the subject perhydrolase includes but is not limited to percaproic acid, percaprylic acid, pernonanoic acid, perdecanoic acid, perdodecanoic acid, permyristic acid, perpalmitic acid, perstearic acid, or peroleic acid. In additional embodiments, multiple substrates find use in the present invention.

In some embodiments, as described in greater detail below, the long chain ester substrate is a $C_6$ to $C_{10}$ substrate or a $C_{11+}$ substrate (e.g., a $C_1$ to $C_{22}$ substrate), depending on the desired peracid. As described in greater detail below, a variety of different long chain ester substrates finds use in the present invention. In some particularly preferred embodiments, the ester substrate is selected from one or more of the following: a caproic acid ester, a caprylic acid ester, a nonanoic acid ester, a decanoic acid ester, a dodecanoic acid ester, a myristic acid ester, a palmitic acid ester, a stearic acid ester, and a oleic acid ester, or any saturated or substituted form thereof. In additional embodiments, multiple esters find use in the present invention.

The perhydrolase enzymes and the peracids of the present invention find use in cleaning, bleaching, and/or disinfecting over broad pH and temperature ranges. In some embodiments, the pH range utilized in this generation is about 4 to about 12. In some alternative embodiments, the temperature range utilized is between about 5° C. and about 90° C. Indeed, some embodiments of the present invention provide advantages over the presently used systems (See e.g., EP Appln. 87-304933.9), in that with the present invention, bleaching is possible at the optimum pH of peracid oxidation, as well as providing bleaching at neutral pH, acidic pHs, and at low temperatures. Long chain peracids are low odor or are odor free. As such, the use of the perhydrolase of the present invention provides certain advantages other systems (e.g., other perhydrolases that are limited to the production of shorter chain peracids that have a significant odor).

While the present invention is described herein most fully in regard to laundry and fabric care, it is not intended that the present invention be limited to these applications. Indeed, the present invention finds use in various settings, particularly those in which bleaching by peracids and/or hydrogen peroxide are desired, including but not limited to laundry, dishwashing, fabric treatment, pulp and paper processing, personal care applications, disinfection and cleaning of hard surfaces. For example, it is contemplated that the compositions of the present invention will find use in bleaching of pulp, including use in methods such as those set forth in U.S. Pat. Nos. 6,569,286, 5,785,812, 6,165,318, and 4,400,237, all of which are herein incorporated by reference.

Historically, sodium perborate, and more recently, sodium percarbonate, have been used as bleaching compounds, particularly in European laundry detergents. These compounds tend to rapidly decompose in aqueous solutions to yield hydrogen peroxide ($H_2O_2$), which is the active bleaching species. As sodium perborate is more active at temperatures above 80° C., and less active in the temperature range of 40-60° C. (i.e., wash temperatures that have become most commonly preferred, as of the 1950s), bleaching activators have been incorporated into laundry detergents that contain sodium perborate. Indeed, most laundry detergents contain bleaching activators. These activators are compounds with O- or N-bounded acetyl groups that are able to react with the strongly nucleophilic hydroperoxy anion to yield peroxyacetic acid. Since the reacting species is hydroperoxy anion, alkaline pHs are essential for the efficient conversion of these activators to peracids. The peroxyacetic acid is decomposed in weakly basic media to form singlet oxygen (See e.g., Hofmann et al., J. Prakt. Chem., 334:293-297 [1992]).

Hydrogen peroxide is a particularly effective bleach at high temperatures (e.g., >40° C.) and pH (>10), conditions that are typically used in washing fabrics in some settings. However, as indicated above, cold water washing is becoming more commonly used and results in less effective bleaching by $H_2O_2$ than the use of hot water. To overcome this low temperature disadvantage, detergent formulations typically include bleach boosters, such as TAED (N,N,N'N'-tetraacetylethylenediamine), NOBS (nonanoyloxybenzene sulfonate), etc. While NOBS combines with $H_2O_2$ to form pernonanoc acid, TAED combines with $H_2O_2$ to form peracetic acid, a peracid species that is more effective than $H_2O_2$ alone. Although it helps the bleaching capability of detergent, the TAED reaction is only approximately 50% efficient, as only two out of the four acetyl groups in TAED are converted to peracids. Additionally, conversion of TAED into peracetic acid by hydrogen peroxide is efficient only at alkaline pHs and high temperatures. Thus, the TAED reaction is not optimized for use in all bleaching applications (e.g., those involving neutral or acidic pHs, and cold water). The present invention provides means to overcome the disadvantages of TAED use. For example, some particularly preferred embodiments of the present invention find use in cold water applications, as well as those involving neutral or acidic pH levels. Furthermore, additional particularly preferred embodiments of the present invention provide means for peracid generation from hydrogen peroxide, with a high perhydrolysis to hydrolysis ratio. Such means provide advantages over compositions that contain enzymes such as esterases and lipases) which have very low perhydrolysis to hydrolysis ratios.

In addition to its applications in detergents, some preferred embodiments of the present invention provide methods and compositions for the use of peracids in textile bleaching and in various other applications. In some embodiments, the present invention provides one-step methods for textile processing applications, including but not limited to one-step desizing, scouring and bleaching processes (See e.g., WO 03/002810, EP 1255888, WO 01/64993, and US 2002/0007516, all of which are hereby incorporated by reference). As described in greater detail herein, in some embodiments, bleaching involves processing textile material before it is dyed and/or after it is incorporated into textile goods. However, it is not intended that the present invention be limited to any particular regimen of use nor any particular textile material.

Furthermore, many peracids find use as an effective bactericide (See, Baldry, J. Appl. Bacteriol., 54:417-423 [1983]). Thus, certain embodiments of the present invention provides compositions and methods for the sterilization/disinfection of various objects, including but not limited to medical devices, medical equipment, industrial equipment, and fermenters, as well as any object that needs to be sterilized and/or disinfected. In additional embodiments, the present invention provides compositions and methods suitable for use in biofilm control, such as in cooling towers.

Also as described in more detail in the Examples below, the present invention provides many advantages for cleaning and/or sterilization of a wide range of objects. In additional embodiments, the present invention provides compositions that are effective in cleaning, bleaching, and disinfecting, over a range of wash temperatures and pHs. In yet further embodiments, the present invention finds use in degradation of peracids through the perhydrolase peracid degradation activity. In some preferred embodiments, this activity is used in peracid waste clean up applications.

Furthermore, certain perhydrolase enzymes of the present invention are active on various acyl donor substrates, as well as being active at low substrate concentrations, and provide means for efficient perhydrolysis due to the high peracid:acid ratio. Indeed, it has been recognized that higher perhydrolysis to hydrolysis ratios are preferred for bleaching applications (See e.g., U.S. Pat. Nos. 5,352,594, 5,108,457, 5,030,240, 3,974,082, and 5,296,616, all of which are herein incorporated by reference). Certain perhydrolase enzymes of the present invention provide perhydrolysis to hydrolysis ratios that are greater than 1. In particular embodiments, the perhydrolase enzymes provide a perhydrolysis to hydrolysis ratio greater than 1 and find use in bleaching.

In addition, the perhydrolases of the present invention have been shown to be active in commonly used detergent formulations (e.g., Ariel Futur, WOB, etc.). Thus, the subject perhydrolase provides many advantages in various cleaning settings.

As indicated above, particular components for peracid production by enzymatic perhydrolysis are enzyme, ester substrate, and hydrogen peroxide. In some embodiments, hydrogen peroxide is added directly in batch, while in other embodiments, it is continuously generated in situ. Current washing powders use batch additions of $H_2O_2$, in the form of percarbonate or perborate salts that spontaneously decompose to $H_2O_2$. The perhydrolase enzymes of the present invention find use in the same washing powder batch method as the $H_2O_2$ source. However, these enzymes also find use with any other suitable source of $H_2O_2$, including $H_2O_2$ generated by chemical, electrochemical, and/or enzymatic means. Examples of chemical sources include, but are not limited to the percarbonates and perborates mentioned above. A non-limiting example of an electrochemical source is a fuel cell fed oxygen and hydrogen gas, while a non-limiting example of an enzymatic example includes production of $H_2O_2$ from the reaction of glucose and oxygen with glucose oxidase. The following equation provides an example of a coupled system that finds use with the present invention.

$$\text{Glucose} + O_2 \xrightarrow{\text{Glucose oxidase}} \text{gluconic acid} + H_2O_2$$

$$H_2O_2 + \text{ester substrate} \xrightarrow{\text{Perhydrolase}} \text{alcohol} + \text{peracid}$$

It is not intended that any embodiments of the present invention be limited to any specific enzyme, as any enzyme that generates $H_2O_2$ with a suitable substrate finds use in the present invention. For example, lactate oxidases from Lactobacillus species which are known to create $H_2O_2$ from lactic acid and oxygen find use in the present invention. Indeed, one advantage of certain methods of the present invention is that the generation of acid (e.g., gluconic acid in the above example) reduces the pH of a basic solution to the pH range in which the peracid is most effective in bleaching (i.e., near the pKa). Other enzymes (e.g., alcohol oxidase, ethylene glycol oxidase, glycerol oxidase, amino acid oxidase, etc.) that can generate hydrogen peroxide also find use with ester substrates in combination with the perhydrolase enzymes of the present invention to generate peracids.

As described in greater detail herein, the present invention provides methods and compositions comprising at least one perhydrolase enzyme for cleaning and other applications. In some embodiments, the present invention provides methods and compositions for generation of long chain peracids. Some preferred embodiments of the present invention find particular use in applications involving cleaning, bleaching and disinfecting.

Compositions comprising a perhydrolase enzyme that perhydrolyzes long chain acyl ester substrates to produce long chain peracids are provided, as well as methods of using the same. In some embodiments, the present invention finds particular use in applications that include cleaning, bleaching and/or disinfecting.

As noted above, the present application claims priority to the patent application WO05/056782. The complete disclosure of WO05/056782, including but not limited to all descriptions of perhydrolase enzymes, amino acid alterations, crystal structures, assay methods, methods of use, sequences, homologs, orthologs, sequence alignments, figures, tables, cleaning compositions, etc., is hereby incorporated by reference herein for all purposes. It is also noted that in some particularly preferred embodiments, the enzymes provided herein hydrolyze, as well as perhydrolyze, long chain acyl ester substrates.

Perhydrolase Enzymes

As indicated above, the present invention provides isolated perhydrolase enzymes that perhydrolyzes long chain acyl ester substrates. In some preferred embodiments in the presence of a long chain acyl ester substrate and hydrogen peroxide, the enzymes produce long and medium chain peracids. In some embodiments, the perhydrolases have an altered substrate specificity relative to a naturally-occurring perhydrolase (e.g., the naturally-occurring perhydrolase of M. smegmatis (SEQ ID NO:2)), in that the subject perhydrolases are capable of perhydrolyzing long chain ethyl ester substrates at a rate that is higher than the rate of hydrolysis for short chain ester substrates. In some particular embodiments, a perhydrolase is capable of perhydrolyze long chain ester substrates at a rate that is at least about 10% greater, at least about 50% greater, at least about 100% greater, at least about 200% greater, at least about 500% greater or at least about 10,000% greater than the perhydrolysis rate for small chain ester substrates. In some embodiments, the long chain ester perhydrolysis rate: short chain ester hydrolysis rate ratio of a subject perhydrolase is at least about 1, at least about 2, at least about 3, at least about 10, at least about 100 or at least about 10,000, where in the short chain ester substrates include peracetic and perbutanoic acid ester and the long chain ester substrate includes peroctanoic acid ester.

Various amino acids in a subject perhydrolase enzyme are referred to herein in reference to their position in the primary amino acid sequence of the enzyme (e.g., "a subject perhydrolase may contain a Gly at position 12"). As described above, and as readily apparent to one of skill in the art, the amino acid positions of a subject perhydrolase enzyme are defined relative to the corresponding position of the perhydrolase of SEQ ID NO:2 (i.e., the perhydrolase of wild type M. smegmatis). In preferred embodiments, corresponding amino acids positions are identified by structural analysis and/or by aligning the primary amino acid sequences of the subject perhydrolase enzyme and SEQ ID NO:2. Methods of aligning the primary amino acid sequence of related enzymes are well known (See e.g., Upton and Buckley, Trends Biochem. Sci., 20:178 [1995]). In addition, non-limiting alignments are provided in WO05/056782.

In some preferred embodiments, the perhydrolases of the present invention have an amino acid sequence that is at least about 35% identical to the amino acid sequence of a parent enzyme (e.g., wild-type enzyme that is encoded by a microorganism, although it is not intended that the present invention be limited to variants of wild-type enzymes, as engineered enzymes find use as parent enzymes). In some embodiments, the perhydrolases of the present invention are related to, but not the same as a wild-type enzyme encoded by the genome of a microorganism. In some particularly preferred embodiments, the perhydrolases of the present invention have an amino acid sequence that is at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 97%, at least about 98%, or at least about 99% to the amino acid of a parental enzyme (e.g., the wild-type perhydrolase of M. smegmatis, or a variant of that perhydrolase set forth in WO 05/05678, or a naturally-occurring acyltransferase-related enzyme encoded by the genome of a bacterium, as set forth in WO 05/05678).

In some preferred embodiments, the amino acid sequence of a perhydrolase of the present invention differs from a parent enzyme by a small number of amino acid residues. The number of differing amino acid residues may be about 1, about 2, about 3, about 4, about 5, at least about 10, at least about 15, at least about 20, at least about 30, at least about 40, at least about 50, or more amino acid residues. In some embodiments, the number of different amino acids between variants is between about 1 and about 10.

In some embodiments, the perhydrolase enzymes of the present invention comprise any one or a combination of the following amino acids: a Gly, Pro or Gln at position 12, a Trp at position 22, a Pro at position 59, a Pro at position 153, a Thr, Ser, Val or Gln at position 154, a Gly at position 194, a Ser, Gln Val, Gly, Pro, Ile or His at position 196, and/or a Tyr or Trp at position 204. In some particularly preferred embodiments, the perhydrolase enzymes of the present invention comprise an: a) Ala at position 154 and a Met at position 194, b) a Gly at position 154 and a Val at position 194, or: c) a Gly at position 12 and a Met at position 194, d) a Thr at position 154 and an Ile at position 196, e) a Gln at position 12 and a Val at position 154, f) a Met at position 12 and a Glu at position 154, g) Gly at position 12 and a Gly at position 154, h) a Glu at position 154 and a Ser at position 194, or i) a Gly at position 12 and a Trp at position 22, or any combination thereof.

Although it is not intended that the present invention be limited to any particular mechanism, the presence of these amino acids provides a perhydrolase that is capable of hydrolyzing long chain acyl esters to produce long chain peracids. In some embodiments, substitution of an amino acid of a wild type perhydrolase with one of the above amino acids produces a perhydrolase with an altered substrate specificity, as compared to the wild type perhydrolase enzyme.

In some embodiments, the perhydrolase enzymes perhydrolyze long chain acyl ester substrates, where an equivalent perhydrolase enzyme that does not contain one or more of the above amino acid substitutions does not detectably perhydrolyze the same substrate(s). In some other embodiments, the perhydrolases of the present invention have a greater specificity for long chain acyl ester substrates than short chain acyl ester substrates.

The structure/function relationship of several perhydrolase enzymes, including the naturally-occurring perhydrolase of M. smegmatis and several hundred active variants thereof and homologous enzymes from other species was investigated in great detail, as described in WO 05/056782. Indeed, it is contemplated that a wide variety of amino acid substitutions be made to a perhydrolase enzyme without abolishing its activity. Further, the specific amino acids described above can be substituted into any perhydrolase to produce a perhydrolase than can produce long chain peracids.

The amino acid coordinates of the naturally-occurring M. smegmatis perhydrolase enzyme and a discussion of the crystal structure of the same are provided in WO 05/056782. Further, as reported in WO 05/056782, the M. smegmatis perhydrolase has been subjected to saturation mutagenesis in order to systematically test the effects of amino acid substitutions at every amino acid position in the enzyme. In these experiments, each amino acid of the M. smegmatis perhydrolase was substituted by each of the remaining 19 amino acids, and each of the variants was systematically tested for various activities, including their hydrolytic activity, their perhydrolytic ("PAF") activity, peracid degradation ("PAD") activity, pH stability, thermal stability, chemical stability, etc. Lists of hundreds of amino acid substitutions that are tolerated by and in certain embodiments may be used to alter the hydrolytic activity, perhydrolytic activity, peracid degradation activity or stability of the M. smegmatis perhydrolase are set forth in WO 05/056782.

In some embodiments of the present invention, any amino acid alterations that confer the ability to perhydrolyze a long chain ester substrate are combined with any of the amino acid alterations described in WO 05/056782, to produce variants of the proteins described by herein. In some embodiments, the amino acid alterations are combined to produce variants that have an increase or decrease in the rate of peracid hydrolysis, and/or an increase or decrease in the perhydrolysis/hydrolysis ratio.

In some preferred embodiments, one or more of amino acid alterations that provide long chain peracids are combined with alterations that provide a perhydrolase having a higher perhydrolysis to hydrolysis ratio (e.g., a ratio of greater than 1.0), and a lower peracid hydrolysis rate (e.g., a peracid hydrolysis rate of less than 0.8, as compared to the SEQ ID NO:2) to provide a perhydrolase enzyme that efficiently produces long chain peracid(s).

In some embodiments, and without any intention to limit any aspect of the invention to any particular sequence, the perhydrolase enzymes of the present invention comprise: a) one or more of the above-described long-chain peracid providing alterations and b) one or more alterations that provides rate of peracid hydrolysis of about 0.8 or less, in comparison with the wild-type M. smegmatis perhydrolase. In some of these embodiments, the one or more alterations that provides a rate of peracid hydrolysis of about 0.8 or less comprises at least one substitution selected from A122, A23, A29, A55, D45, D62, D65, E26, E50, F150, F46, G110, G124, G43, L109, L119, L42, L68, L78, L82, L84, N59, P66, R101, R27, R4, R67, S112, S54, S76, T116, T120, T25, V125, V48, W149, Y73, A44, A79, D85, E51, G124, G126, G15, G52, I194, K97, L119, L12, L38, L53, L68, L86, N94, P18, R101, R27, R4, R67, S54, S72, T58, T80, V118, V87, W34, R4, I5, D10, L12, W14, V19, T25, W34, I49, E50, E51, L53, S54, A55, R56, N59, D62, T64, D65, R67, L68, N69, S76, C77, T80, L82, P83, L86, V87, N94, T96, F100, R101, L109, M111, L114, L119, W149, Y1d29, A122, G126, T127, A23, A55, A79, D65, D85, E26, F154, G110, G124, G126, G22, G36, G43, G52, G70, I49, K97, L109, L114, L119, L12, L38, L42, L53, L68, L86, P104, P83, Q41, R102, R56, R67, S54, T57, V118, V125, W14, W149, Y129, Y73, A122, A23, A79, D45, D65, D85, E26, E47, E51, F150, F196, F28, G110, G124, G36, G43, G52, G70, I107, I5, I60, L109, L119, L53, L6, L68, L82, M111, P104, P66, R102, R67, S11, S112, S121, S54, S72, T25, T35, T57, T58, V118, V125, V19, W149, W16, A108, A122, A23, A29, A79, C7, D106, D21, D45, D62, D65, D85, E50, F150, F28, G124, G126, G22, G36, G52, I107, I194, K97, L105, L109, L114, L119, L38, L68, L78, L82, L84, M111, N69, N94, P104, P63, P66, R102, R27, S11, S112, S54, S72, T116, T120, T127, T13, T25, T57, T80, T96, V113, A122, A29, A71, A79, C7, D106, D21, D61, D65, D85, E47, E50, F150, F196, F28, F46, G124, G126, G15, G36, G70, I49, I5, I60, L105, L109, L12, L38, L42, L53, L84, L86, M111, N59, P146, P24, P66, Q41, R102, R27, R56, S112, S121, S54, S72, T116, T120, T127, T128, T13, T57, T64, V125, V17, V19, W14, W149, W16, Y129, Y99, A108, A122, A23, A29, A44, A55, A71, A79, C77, D45, D61, D65, D85, D95, E47, E51, F150, F196, F46, G110, G126, G36, G43, G52, I107, I194, I49, I5, I60, I89, L114, L42, L53, L68, L78, L84, M111, N59, N94, P146, P24, P30, P63, P66, P83, Q117, R101, R4, S112, S121, S72, T116, T120, T127, T13, T57, T96, V113, V125, V17, V19, V32, V87, W149, Y129, Y73, G190, V191, G193, T197, N201, D203, L208, A209, V212, L215, and L216. In some embodiments, the one or more alterations provide(s) a ratio of peracid hydrolysis of about 0.1 or less, which alteration is at least one substitution selected from R4, L12, G15, P18, R27, W34L38, A44, E51, G52, L53, S54, T58, R67, L68, S72, A79, T80, D85, L86, V87, N94, K97, R101, V118, L119, G124, G126, and I194.

In further embodiments and again without any intention to limit any aspect of the present invention to any particular sequence, the perhydrolase enzymes of the present invention comprise: a) one or more of the above-described long-chain peracid providing alterations, and b) one or more alterations that provides a change in perhydrolysis, such that the ratio of variant perhydrolase perhydrolysis to wild-type perhydrolase perhydrolysis is at least about 1.2. In some of these embodiments, the one or more alterations that provides one or more alterations that provides a change in perhydrolysis, such that the ratio of variant perhydrolase perhydrolysis to wild-type perhydrolase perhydrolysis is at least about 1.2 is selected from C7, D10, L12, G15, P18, V19, G22, T25, E26, R27, F28, A29, P30, D31, G36, Q40, Q41, L42, G43, A44, D45, F46, E47, I49, E51, L53, S54, A55, T57, D61, P63, T64, D65, P66, R67, L68, N69, A71, S72, Y73, S76, L78, A79, T80, L82, P83, D85, L86, D95, K97, R101, T103, P104, L105, D106, I107, L109, M111, V113, Q117, V118, S121, G124, V125, G126, T127, P148, F150, I153, F154, and F196. In some preferred embodiments, the one or more alterations provide a change in perhydrolysis, such that the ratio of variant perhydrolase perhydrolysis to wild-type perhydrolase perhydrolysis is at least about 2, which alterations are selected from A44, C7, D10, D85, D95, E26, E47, I107, L12, L42, P104, P148, S54, Q40, Q117, D203, V206, E210, K97, L12, P104, V125, D85, L53 and L78.

In some alternative preferred embodiments, and again without any intention to limit any aspect of the invention to any particular sequence, the perhydrolase enzymes of the present invention comprise one or more of the above-described long-chain providing alterations, as well as amino acid substitutions that provide a perhydrolase that exhibits perhydrolysis activity ratio of at least about 1.2, and a peracid hydrolysis activity ratio of about 0.8 or less, as compared to wild-type perhydrolase. In some of these embodiments, the substitutions are selected from A29, A44, A55, A71, A79, C7, D10, D106, D31, D85, E26, E47, F150, F154, F196, F28, G124, G126, G36, G43, I153, L109, L42, L53, L109, L42, L53, L109, L42, L53, L68, L82, L86, M111, N69, P104, P148, P18, P63, P66, P83, Q117, Q40, R101, R67, S54, S121, S72, S76, T25, T64, V115, and V19. In some preferred embodiments, the following amino acid substitutions are employed: L12I and S54V, L12M and S54T, L12T and S54V, L12Q, T25S and S54V, L53H and S54V, S54P and V125R, S54V and V125G, S54V and F196G, S54V, K97R and V125G, and A55G, R67T, K97R, and V125G, as described in WO 05/056782.

Amino acids that are critical for the activity of the subject perhydrolase are described in WO 05/056782, as are amino acids that are suitable for alteration in a perhydrolase without abolishing its activity. Also, WO 05/056782 describes several perhydrolase enzymes from species other then M. smegmatis, as well as domains that are conserved in this family of perhydrolases, including, but not limited to Agrobacterium rhizogenes (Q9 KWA6), A. rhizogenes (Q9 KWB 1), A. tumefaciens (Q8UFG4), A. tumefaciens (Q8UAC0), A. tumefaciens (Q9ZI09), A. tumefaciens (ACA), Prosthecobacter dejongeii (RVM04532), Rhizobium. loti (Q98MY5), R. meliloti (Q92XZ1), R. meliloti (Q9EV56), R. rhizogenes (NF006), R. rhizogenes (NF00602875), R. solanacerarum (Q8XQI0), Sinorhizobium meliloti (RSM02162), S. meliloti (RSM05666), Mesorhizobium loti (RMLO00301), A. rhizogenes (Q9 KWA6), A. rhizogenes (Q9 KWB1), Agrobacterium tumefaciens (AAD02335), Mesorhizobium loti (Q98MY5), Mesorhizobium loti (ZP00197751), Ralstonia solanacearum (Q8XQI0), Ralstonia eutropha (ZP00166901), Moraxella bovis (AAK53448), Burkholderia cepacia (ZP00216984), Chromobacterium violaceum (Q7NRP5), Pirellula sp. (NP_865746), Vibrio vulnificus (AA007232), Salmonella typhimurium (AAC38796), Sinorhizobium meliloti (SMa1993), Sinorhizobium meliloti (Q92XZ1) and Sinorhizobium meliloti (Q9EV56). The amino acid sequences of these proteins, the sequence alignments, and all other information relating to the above is incorporated by reference herein for all purposes from WO 05/056782.

In some particularly preferred embodiments, the perhydrolase enzyme is a GDSL-GRTT/ARTT (SEQ ID NO:28-30, respectively) or SGNH hydrolase (SEQ ID NO:31), as described in WO 05/056782. In some embodiments, the enzyme comprises at least one or a combination of the following conserved residues: L6, W14, W34, L38, R56, D62, L74, L78, H81, P83, M90, K97, G110, L114, L135, F180, and G205.

As described in WO 05/056782, various methods find use determining the activity(ies) of a perhydrolase enzyme. However, it is not intended that the present invention be limited to any particular assay method.

Suitable reporter substrates for determining whether a perhydrolase can employ long chain ethyl substrates include, but are not limited to p-nitrophenylesters containing at least a $C_6$ carbon chain (e.g., p-nitrophenylcaproate, p-nitrophenylcaprylate, p-nitrophenylnonanoate, p-nitrophenyldecanoate, p-nitrophenyldodecanoate acid, p-nitrophenylmyristate, p-nitrophenylpalmitate, p-nitrophenylstearate, and p-nitrophenyloleate). Additional long chain ester substrates that find use include, but are not limited to: hexanoate esters, heptanoate esters, octanoate esters, nonanoate esters, and esters of higher carboxylic acids such as C10 thru C18 or higher.

Perhydrolase Production

The wild type M. smegmatis perhydrolase is an intracellular protein in its native host. In some embodiments, the perhydrolase enzymes of the present invention perhydrolase are produced intracellularly in non-native hosts. In some embodiments, a signal sequence is added to the perhydrolase, which facilitates expression of the perhydrolase by secretion into the periplasm (i.e., in Gram-negative organisms, such as E. coli), or into the extracellular space (i.e., in Gram-positive organisms, such as Bacillus and Actinomyces), or fungal hosts (e.g., Trichoderma, Aspergillus, Saccharomyces, and Pichia). It is not intended that the present invention be limited to these specific hosts, as various other organisms, including other prokaryotes and eukaryotes find use as expression hosts in the present invention.

A variety of commercially available expression systems, including but not limited to pBAD, plac, T7, find use in the expression of the perhydrolase in Gram-negative hosts (e.g., E. coli). In some embodiments, the same types of promoters find use in another Gram-negative host, Pantoea citrea.

Bacillus species are well-known as suitable hosts for expression of extracellular proteins (e.g., proteases). Intracellular expression of proteins is less well known. IN some embodiments, expression of the perhydrolase protein intracellularly in B. subtilis is accomplished using any variety of promoters, including, but not limited to pVeg, pSPAC, pAprE, or pAmyE in the absence of a signal sequence on the 5' end of the gene. In some embodiments, expression is achieved from a replicating plasmid (high or low copy number), while in alternative embodiments, expression is achieved by integrating the desired construct into the chromosome. Integration can be done at any locus, including but not limited to the aprE, amyE, or pps loci. In some embodiments, the perhydrolase is expressed from one or more copies of the integrated construct. In alternative embodiments, multiple integrated copies are obtained by the integration of a construct capable of amplification (e.g., linked to an antimicrobial cassette and flanked by direct repeat sequences), or by ligation of multiple copies and subsequent integration into the chromosome. In some embodiments, expression of the perhydrolase with either the replicating plasmid or the integrated construct is monitored using the pNB activity assay (described herein) in an appropriate culture.

As with Bacillus, in some embodiments, expression of the perhydrolase in Streptomyces is done using a replicating plasmid, while in other embodiments, expression of the perhydrolase is accomplished via integration of the vector into the Streptomyces genome. Any promoter capable of being recognized in Streptomyces finds use in driving transcription of the perhydrolase gene (e.g., glucose isomerase promoter, or the A4 promoter). Replicating plasmids, either shuttle vectors or Streptomyces only, also find use in the present invention for expression (e.g., pSECGT).

In some preferred embodiments, the perhydrolases of the present invention are secreted from the host cell such that the perhydrolase can be recovered from the culture medium in which the host cell is cultured.

Cleaning Compositions

As indicated above, the present invention provides cleaning compositions comprising the long chain perhydrolase enzymes of the present invention. In some embodiments, the cleaning compositions comprise at least one perhydrolase of the present invention, at least one long chain ester substrate, and at least one source of hydrogen peroxide. In some preferred embodiments, the long chain ester substrate has the formula $R_1C(=O)OR_2$, wherein $R_1$ comprises a substituted or unsubstituted carbon chain of at least 5 carbon atoms and $R_2$ is any organic moiety. The ester substrate and source of hydrogen peroxide are described in greater detail herein. Also, in many embodiments, a variety of other compounds are present in the cleaning compositions of the present invention.

In some embodiments, the cleaning compositions of the present invention find use in laundry applications, hard surface cleaning, and/or automatic dishwashing applications, as well as personal care/cosmetic applications (e.g., for cleaning of dentures, teeth, hair and skin). However, due to their unique properties of increased effectiveness in lower temperature solutions and the superior color-safety profile, the perhydrolase enzymes of the present invention are ideally suited for laundry applications (e.g., the bleaching of fabrics). Furthermore, the enzymes of the present invention find use in granular and/or liquid compositions, including gels and emulsions.

The perhydrolase enzymes of the present invention also find use in cleaning additive products. In some preferred embodiments, the cleaning additive products are ideally suited for inclusion in wash processes where additional bleaching effectiveness is desired. Such instances include, but are not limited to low temperature solution cleaning applications. In some embodiments, the additive products are, in their simplest form, one or more of the enzymes of the present invention. In some embodiments, the additive is packaged in dosage form for addition to a cleaning process where a source of peroxygen is employed and increased bleaching effectiveness is desired. Such single dosage forms include, but are not limited to pills, tablets, gelcaps or other single dosage units (e.g., pre-measured powders or liquids). In some embodiments, at least one filler and/or carrier material is included in order to increase the volume of the cleaning composition. Suitable filler or carrier materials include, but are not limited to, various salts of sulfate, carbonate and silicate as well as talc, clay, etc. In some embodiments, filler and/or carrier materials for liquid compositions comprise water or low molecular weight primary and secondary alcohols including polyols and diols. Examples of such alcohols include, but are not limited to, methanol, ethanol, propanol and isopropanol. In some embodiments, the compositions contain from about 5% to about 90% of such materials. In yet further embodiments, acidic fillers are used to reduce pH. In some alternative embodiments, the cleaning, additive(s) include activated peroxygen source such as esters of alcohols, esters of diols, or esters of polyols. In yet additional embodiments, the cleaning additives comprise one or more adjunct ingredients.

The cleaning compositions and cleaning additives of the present invention require an effective amount of the enzyme provided by the present invention. In some particularly preferred embodiments, the cleaning compositions of the present invention comprise at least 0.0001 weight percent, from about 0.0001 to about 1, from about 0.001 to about 0.5, or even from about 0.01 to about 0.1 weight percent of at least one perhydrolase enzyme of the present invention.

In addition to typical cleaning compositions, it is readily understood that perhydrolase variants of the present invention find use in any purpose that the native or wild-type enzyme is used. Thus, such variants find use for example, in bar and liquid soap applications, dishcare formulations, surface cleaning applications, contact lens cleaning solutions and/or products, waste treatment, textile applications, pulp-bleaching, disinfectants, skin care, oral care, hair care, etc. Indeed, it is not intended that any variants of the perhydrolase of the present invention be limited to any particular use. For example, in some embodiments, the variant perhydrolases of the present invention comprise, in addition to decreased allergenicity, enhanced performance in a detergent composition (as compared to the wild-type or unmodified perhydrolase).

Source of Hydrogen Peroxide

In some embodiments, the cleaning compositions of the present invention comprise a source of hydrogen peroxide, which can be hydrogen peroxide itself or a composition that produces hydrogen peroxide as a reaction product. Suitable hydrogen peroxide sources that produce hydrogen peroxide as a reaction product include, but are not limited to a peroxygen source selected from:

(i) from about 0.01 to about 50, from about 0.1 to about 20, or from about 1 to 10 weight percent of a per-salt, an organic peroxyacid, urea hydrogen peroxide and mixtures thereof;

(ii) from about 0.01 to about 50, from about 0.1 to about 20, or from about 1 to 10 weight percent of a carbohydrate and from about 0.0001 to about 1, from about 0.001 to about 0.5, from about 0.01 to about 0.1 weight percent carbohydrate oxidase; and (iii) mixtures thereof.

Suitable per-salts include, but are not limited to those selected from alkalimetal perborate, alkalimetal percarbonate, alkalimetal perphosphates, alkalimetal persulphates and mixtures thereof.

In some preferred embodiments, the carbohydrate is selected from mono-carbohydrates, di-carbohydrates, tri-carbohydrates, oligo-carbohydrates and mixtures thereof. Suitable carbohydrates include carbohydrates selected from the group consisting of D-arabinose, L-arabinose, D-cellobiose, 2-deoxy-D-galactose, 2-deoxy-D-ribose; D-fructose, L-fucose, D-galactose, D-glucose, D-glycero-D-gulo-heptose, D-lactose, D-lyxose, L-lyxose, D-maltose, D-mannose, melezitose, L-melibiose, palatinose, D-raffinose, L-rhamnose, D-ribose, L-sorbose, stachyose, sucrose, D-trehalose, D-xylose, L-xylose and mixtures thereof. Indeed, it is not intended that the present invention be limited to any particular carbohydrate, as various carbohydrates find use in the present invention.

Suitable carbohydrate oxidases include, but are not limited to carbohydrate oxidases selected from aldose oxidase (IUPAC classification EC1.1.3.9), galactose oxidase (IUPAC classification EC1.1.3.9), cellobiose oxidase (IUPAC classification EC1.1.3.25), pyranose oxidase (IUPAC classification EC1.1.3.10), sorbose oxidase (IUPAC classification EC1.1.3.11) and/or hexose oxidase (IUPAC classification EC1.1.3.5), glucose oxidase (IUPAC classification EC1.1.3.4) and mixtures thereof.

Ester Substrates

In some embodiments, at least one ester substrate comprising aliphatic and/or aromatic carboxylic acids and alcohols is utilized with at least one perhydrolase enzyme of the present invention. In some embodiments, the substrate is selected from one or more of the following: caproic acid ester, caprylic acid ester, nonanoic acid ester, decanoic acid ester, dodecanoic acid ester, myristic acid ester, palmitic acid ester, stearic acid ester, and oleic acid ester, as well as longer chain ester substrates.

In some preferred embodiments, the ester substrate is present in an amount that is from about 0.01 to about 99.9, from about 0.01 to about 50, from about 0.1 to 20, or from about 1 to about 15 weight percent of the cleaning composition.

In some embodiments, suitable molecules comprising an ester moiety have the formula:

$$R^1O_x[(R^2)_m(R^3)_n]_p$$

wherein $R^1$ is a moiety selected from the group consisting of H or a substituted or unsubstituted alkyl, heteroalkyl, alkenyl, alkynyl, aryl, alkylaryl, alkylheteroaryl, and heteroaryl; in some embodiments of the present invention, $R^1$ comprises from 1 to 50,000 carbon atoms, from 1 to 10,000 carbon atoms, or from 2 to 100 carbon atoms;

each $R^2$ is an optionally substituted alkoxylate moiety, in some embodiments of the present invention, each $R^2$ is independently an ethoxylate, propoxylate or butoxylate moiety;

$R^3$ is an ester-forming moiety having the formula:

$R^4CO$— wherein $R^4$ is selected from H, substituted or unsubstituted alkyl, alkenyl, alkynyl, aryl, alkylaryl, alkylheteroaryl, and heteroaryl, in some embodiments of the present invention, while in other embodiments, $R^4$ is a substituted or unsubstituted straight or branched chain alkyl, alkenyl, or alkynyl, moiety comprising from 5 to 22 or more carbon atoms, an aryl, alkylaryl, alkylheteroaryl, or heteroaryl moiety comprising from 5 to 12 or more carbon atoms, or $R^4$ is a substituted or unsubstituted $C_5$-$C_{10}$ or longer alkyl moiety, or $R^4$ is a substituted or unsubstituted $C_{11}$-$C_{22}$ or longer alkyl moiety;

x is 1 when $R^1$ is H; when $R^1$ is not H, x is an integer that is equal to or less than the number of carbons in $R^1$ p is an integer that is equal to or less than x m is an integer from 0 to 50, an integer from 0 to 18, or an integer from 0 to 12, and n is at least 1.

In some embodiments of the present invention, the molecule comprising an ester moiety is an alkyl ethoxylate or propoxylate having the formula $R^1O_x[(R^2)_m(R^3)_n]_p$ wherein:

$R^1$ is an $C_2$-$C_{32}$ substituted or unsubstituted alkyl or heteroalkyl moiety;

each $R^2$ is independently an ethoxylate or propoxylate moiety;

$R^3$ is an ester-forming moiety having the formula:

$R^4CO$— wherein $R^4$ is selected from H, substituted or unsubstituted alkyl, alkenyl, alkynyl, aryl, alkylaryl, alkylheteroaryl, and heteroaryl, in some embodiments of the present invention, while in other embodiments, $R^4$ is selected from a substituted or unsubstituted straight or branched chain alkyl, alkenyl, or alkynyl moiety comprising from 5 to 22 or more carbon atoms, a substituted or unsubstituted aryl, alkylaryl, alkylheteroaryl, or heteroaryl moiety comprising from 5 to 12 carbon or longer atoms or $R_4$ is a substituted or unsubstituted $C_5$-$C_{10}$ or longer alkyl moiety, or $R_4$ is a substituted or unsubstituted $C_5$-$C_{22}$ or longer alkyl moiety;

x is an integer that is equal to or less than the number of carbons in $R^1$ p is an integer that is equal to or less than x m is an integer from 1 to 12, and n is at least 1.

In some embodiments of the present invention, the molecule comprising the ester moiety has the formula:

$$R^1O_x[(R^2)_m(R^3)_n]_p$$

wherein $R^1$ is H or a moiety that comprises a primary, secondary, tertiary or quaternary amine moiety, said $R^1$ moiety that comprises an amine moiety being selected from substituted or unsubstituted alkyl, heteroalkyl, alkenyl, alkynyl, aryl, alkylaryl, alkylheteroaryl, and heteroaryl; in some embodiments, $R^1$ comprises from 1 to 50,000 carbon atoms, from 1 to 10,000 carbon atoms, or from 2 to 100 carbon atoms;

each $R^2$ is an alkoxylate moiety, in some embodiments of the present invention each $R^2$ is independently an ethoxylate, propoxylate or butoxylate moiety;

$R^3$ is an ester-forming moiety having the formula:

$R^4CO$— wherein $R^4$ is selected from H, substituted or unsubstituted alkyl, alkenyl, alkynyl, aryl, alkylaryl, alkylheteroaryl, and heteroaryl, in some embodiments of the present invention, in other embodiments, $R^4$ is selected from substituted or unsubstituted straight or branched chain alkyl, alkenyl, or alkynyl moiety comprising from 5 to 22 carbon atoms, a substituted or unsubstituted aryl, alkylaryl, alkylheteroaryl, or heteroaryl moiety comprising from 9 to 12 or more carbon atoms or $R_4$ is a substituted or unsubstituted $C_5$ -$C_{10}$ or longer alkyl moiety, or $R_4$ is a substituted or unsubstituted $C_{11}$-$C_{22}$ or longer alkyl moiety;

x is 1 when $R^1$ is H; when $R^1$ is not H, x is an integer that is equal to or less than the number of carbons in $R^1$ p is an integer that is equal to or less than x m is an integer from 0 to 12 or even 1 to 12, and n is at least 1.

In any of the aforementioned embodiments of the present invention, the molecule comprising an ester moiety may have a weight average molecular weight of less than 600,000 Daltons, less than 300,000 Daltons, less than 100,000 Daltons or even less than 60,000 Daltons.

Suitable molecules that comprise an ester moiety include, but are not limited to polycarbohydrates that comprise an ester moiety.

Adjunct Materials

While not essential for use of the present invention, the non-limiting list of adjuncts illustrated hereinafter are suitable for use in the cleaning compositions of the present invention. In some embodiments, these materials are incorporated to assist or enhance cleaning performance, for treatment of the substrate to be cleaned, or to modify the aesthetics of the cleaning composition as is the case with perfumes, colorants, dyes or the like. It is understood that such adjuncts are in addition to the enzymes of the present invention, hydrogen peroxide source and ester substrate. The precise nature of these additional components, and levels of incorporation thereof, will depend on the physical form of the composition and the nature of the cleaning operation for which it is to be used. Suitable adjunct materials include, but are not limited to, surfactants, builders, chelating agents, dye transfer inhibiting agents, deposition aids, dispersants, additional enzymes, and enzyme stabilizers, catalytic materials, bleach activators, bleach boosters, preformed peracids, polymeric dispersing agents, clay soil removal/anti-redeposition agents, brighteners, suds suppressors, dyes, perfumes, structure elasticizing agents, fabric softeners, carriers, hydrotropes, processing aids and/or pigments. In addition to the disclosure below, suitable examples of such other adjuncts and levels of use are found in U.S. Pat. Nos. 5,576,282, 6,306,812, and 6,326,348, herein incorporated by reference. In some embodiments, the aforementioned adjunct ingredients constitute the balance of the cleaning compositions of the present invention.

Surfactants—In some embodiments, the cleaning compositions provided by the present invention comprise at least one surfactant or surfactant system wherein the surfactant is selected from nonionic surfactants, anionic surfactants, cationic surfactants, ampholytic surfactants, zwitterionic surfactants, semi-polar nonionic surfactants and mixtures thereof.

In some preferred embodiments, the surfactant is typically present at a level of from about 0.1% to about 60%, from about 1% to about 50% or even from about 5% to about 40% by weight of the subject cleaning composition.

A number of known compounds are suitable surfactants useful in compositions comprising the perhydrolase enzymes of the present invention. These include nonionic, anionic, cationic, anionic or zwitterionic detergents (See e.g., U.S. Pat. Nos. 4,404,128 and 4,261,868). A suitable detergent formulation is that described in U.S. Pat. No. 5,204,015 (incorporated by reference). Those in the art are familiar with the different formulations which find use as cleaning compositions.

As indicated above, in some preferred embodiments, the detergent compositions of the present invention employ a surface active agent (i.e., surfactant) including anionic, nonionic and ampholytic surfactants well known for their use in detergent compositions. Some surfactants suitable for use in the present invention are described in British Patent Application No. 2 094 826 A, incorporated herein by reference. In some embodiments, mixtures of surfactants are used in the present invention.

Suitable anionic surfactants for use in the detergent composition of the present invention include, but are not limited to linear or branched alkylbenzene sulfonates; alkyl or alkenyl ether sulfates having linear or branched alkyl groups or alkenyl groups; alkyl or alkenyl sulfates; olefin sulfonates; alkane sulfonates and the like. Suitable counter ions for anionic surfactants include, but are not limited to alkali metal ions such as sodium and potassium; alkaline earth metal ions such as calcium and magnesium; ammonium ion; and alkanolamines having 1 to 3 alkanol groups of carbon number 2 or 3.

Ampholytic surfactants that find use in the present invention include, but are not limited to quaternary ammonium salt sulfonates, betaine-type ampholytic surfactants, and the like. Such ampholytic surfactants have both the positive and negative charged groups in the same molecule.

Nonionic surfactants that find use in the present invention generally comprise polyoxyalkylene ethers, as well as higher fatty acid alkanolamides or alkylene oxide adduct thereof, fatty acid glycerine monoesters, and the like.

In some preferred embodiments, the surfactant or surfactant mixture included in the detergent compositions of the present invention is provided in an amount from about 1 weight percent to about 95 weight percent of the total detergent composition and preferably from about 5 weight percent to about 45 weight percent of the total detergent composition. As indicated herein, in various embodiments of the present invention, numerous other components are included in the compositions of the present invention. However, it is not intended that the present invention be limited to these specific examples. Indeed, it is contemplated that additional compounds will find use in the present invention. The descriptions below merely illustrate some optional components.

Proteins, particularly the perhydrolase of the present invention can be formulated into known powdered and liquid detergents having pH between 3 and 12.0, at levels of about 0.001 to about 5% (preferably 0.1% to 0.5%) by weight. In some embodiments, these detergent cleaning compositions further include other enzymes such as proteases, amylases, mannanases, peroxidases, oxido reductases, cellulases, lipases, cutinases, pectinases, pectin lyases, xylanases, and/or endoglycosidases, as well as builders and stabilizers.

The addition of proteins to conventional cleaning compositions does not create any special use limitations. In other words, any temperature and pH suitable for the detergent are also suitable for the present compositions, as long as the pH is within the range in which the enzyme(s) is/are active, and the temperature is below the described protein's denaturing temperature. In addition, proteins of the invention find use in cleaning, bleaching, and disinfecting compositions without detergents, again either alone or in combination with a source of hydrogen peroxide, an ester substrate (e.g., either added to or inherent in the system utilized, such as with stains that contain esters, pulp that contains esters etc), other enzymes, surfactants, builders, stabilizers, etc. Indeed it is not intended that the present invention be limited to any particular formulation or application.

Builders—The cleaning compositions of the present invention may comprise one or more detergent builders or builder systems. When a builder is used, the cleaning composition typically comprises at least about 1%, from about 3% to about 60%, or from about 5% to about 40% builder by weight of the cleaning composition.

Builders include, but are not limited to, the alkali metal, ammonium and alkanolammonium salts of polyphosphates, alkali metal silicates, alkaline earth and alkali metal carbonates, aluminosilicate builders polycarboxylate compounds, ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, citric acid, oxydisuccinic acid, polymaleic acid, benzene 1,3,5-tricarboxylic acid, carboxymethyloxysuccinic acid, and soluble salts thereof.

Chelating Agents—In some embodiments, the cleaning compositions provided herein contain at least one chelating agent. Suitable chelating agents include but are not limited to copper, iron and/or manganese chelating agents and mixtures thereof.

When a chelating agent is used, the cleaning composition typically comprises from about 0.1% to about 15%, or from about 3.0% to about 10% chelating agent by weight of the subject cleaning composition.

Deposition Aid—In some embodiments, the cleaning compositions provided herein further comprise at lease one deposition aid. Suitable deposition aids include, but are not limited to polyethylene glycol, polypropylene glycol, polycarboxylate, soil release polymers such as polyterephthalic acid, clays such as kaolinite, montmorillonite, atapulgite, illite, bentonite, halloysite, and mixtures thereof.

Dye Transfer Inhibiting Agents—In yet some further embodiments, the cleaning compositions of the present invention also comprise one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof.

When present in a subject cleaning composition, the dye transfer inhibiting agents are typically present at levels from about 0.0001% to about 10%, from about 0.01% to about 5%, or from about 0.1% to about 3% by weight of the cleaning composition.

Dispersants—In some additional embodiments, the cleaning compositions of the present invention comprise dispersants. Suitable water-soluble organic materials include, but are not limited to the homo- or co-polymeric acids or their salts, in which the polycarboxylic acid comprises at least two carboxyl radicals separated from each other by not more than two carbon atoms.

Enzymes—In some further embodiments, the cleaning compositions of the present invention comprise one or more detergent enzymes which provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, keratinases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. A typical combination is cocktail of conventional applicable enzymes like protease, lipase, cutinase and/or cellulase in conjunction with amylase.

Enzyme Stabilizers—Enzymes for use in detergents can be stabilized by various techniques. The enzymes employed herein can be stabilized by the presence of water-soluble sources of calcium and/or magnesium ions in the finished compositions that provide such ions to the enzymes. It is contemplated that enzyme stabilizers will find use in some embodiments of the cleaning compositions provided herein.

Catalytic Metal Complexes—In some embodiments, the cleaning compositions of the present invention comprise catalytic metal complexes. One type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra (methylenephosphonic acid) and water-soluble salts thereof. Examples of these catalysts are described in U.S. Pat. No. 4,430,243, herein incorporated by reference.

In some embodiments, the compositions provided herein are catalyzed by means of a manganese compound. Such compounds and levels of use are well known in the art and include, for example, the manganese-based catalysts disclosed in U.S. Pat. No. 5,576,282, which is herein incorporated by reference.

Cobalt bleach catalysts useful herein are known, and are described, for example, in U.S. Pat. No. 5,597,936; and U.S. Pat. No. 5,595,967, both of which are incorporated herein by reference. Such cobalt catalysts are readily prepared by known procedures, such as taught for example in U.S. Pat. No. 5,597,936, and U.S. Pat. No. 5,595,967.

In some embodiments, the compositions provided herein also comprise at least one transition metal complex of a macropolycyclic rigid ligand ("MRL"). As a practical matter, and not by way of limitation, in some embodiments of the compositions and cleaning processes provided herein are adjusted to provide on the order of at least one part per hundred million of the active MRL species in the aqueous washing medium, and will preferably provide from about 0.005 ppm to about 25 ppm, more preferably from about 0.05 ppm to about 10 ppm, and most preferably from about 0.1 ppm to about 5 ppm, of the MRL in the wash liquor.

Preferred transition-metals in the instant transition-metal bleach catalyst include manganese, iron and chromium. Preferred MRLs herein are a special type of ultra-rigid ligand that is cross-bridged such as 5,12-diethyl-1,5,8,12-tetraazabicyclo[6.6.2]hexadecane.

Suitable transition metal MRLs are readily prepared by known procedures, such as taught for example in WO 00/332601, and U.S. Pat. No. 6,225,464, both of which are incorporated by reference herein.

Cleaning and Detergent Formulations

The detergent compositions of the present invention are provided in any suitable form, including but not limited to liquids, granules, emulsions, gels, and pastes. When a solid detergent composition is employed, the detergent is preferably formulated in the form of granules. Preferably, the granules are formulated to additionally contain a protecting agent (See e.g., U.S. application Ser. No. 07/642,669 filed Jan. 17, 1991, incorporated herein by reference). Likewise, in some embodiments, the granules are formulated so as to contain materials to reduce the rate of dissolution of the granule into the wash medium (See e.g., U.S. Pat. No. 5,254,283, incorporated herein by reference). In addition, the perhydrolase enzymes of the present invention find use in formulations in which substrate and enzyme are present in the same granule. Thus, in some embodiments, the efficacy of the enzyme is increased by the provision of high local concentrations of enzyme and substrate (See e.g., U.S. Patent Appln. Publ. No. US 2003/0191033, herein incorporated by reference).

The cleaning compositions of the present invention are formulated into any suitable form and prepared by any process chosen by the formulator, non-limiting examples of which are described in U.S. Pat. No. 5,879,584, U.S. Pat. No. 5,691,297, U.S. Pat. No. 5,574,005, U.S. Pat. No. 5,569,645, U.S. Pat. No. 5,565,422, U.S. Pat. No. 5,516,448, U.S. Pat. No. 5,489,392, and U.S. Pat. No. 5,486,303; all of which are incorporated herein by reference.

The cleaning compositions provided herein are typically be formulated such that, during use in aqueous cleaning operations, the wash water will have a pH of from about 5.0 to about 11.5, or from about 7.5 to about 10.5. Liquid product formulations are typically formulated to have a pH from 15 about 3.0 and about 9.0. Granular laundry products are typically formulated to have a pH from about 9 to about 11. Techniques for controlling pH at recommended usage levels include the use of buffers, alkalis, acids, etc., and are well known to those skilled in the art.

When the enzyme(s) of the present invention is/are employed in a granular composition or liquid, it is sometimes desirable for the enzyme(s) to be in the form of an encapsulated particle to protect such enzyme from other components of the granular composition during storage. In addition, encapsulation is also a means of controlling the availability of the enzyme(s) during the cleaning process and may enhance performance of the enzyme(s). In this regard, the enzyme(s) are encapsulated with any suitable encapsulating material known in the art.

The encapsulating material typically encapsulates at least part of the enzyme(s). Typically, the encapsulating material is water-soluble and/or water-dispersible. The encapsulating material may have a glass transition temperature (Tg) of 0° C. or higher (See e.g., WO 97/11151, incorporated herein by reference).

In some embodiments, the encapsulating is selected from carbohydrates, natural or synthetic gums, chitin and chitosan, cellulose and cellulose derivatives, silicates, phosphates, borates, polyvinyl alcohol, polyethylene glycol, paraffin waxes and combinations thereof. When the encapsulating material is a carbohydrate, it is typically selected from monosaccharides, oligosaccharides, polysaccharides, and combinations thereof. Typically, the encapsulating material is a starch. Suitable starches are described in EP 0 922 499, U.S. Pat. No. 4,977,252, U.S. Pat. No. 5,354,559, and U.S. Pat. No. 5,935,826, each of which is herein incorporated by reference.

In some embodiments, the encapsulating material is a microsphere made from plastic (e.g., thermoplastics, acrylonitrile, methacrylonitrile, polyacrylonitrile, polymethacrylonitrile and mixtures thereof). Commercially available microspheres that find use include but are not limited to those supplied by Expancel (Stockviksverken, Sweden) under the trademark EXPANCEL®, and those supplied by PQ Corp. (Valley Forge, Pa.) under the tradenames PM 6545, PM 6550, PM 7220, PM 7228, EXTENDOSPHERES®, LUXSIL®, Q-CEL® and SPHERICEL®.

In addition to the ingredients described above, perfumes, buffers, preservatives, dyes and the like also find use with the present invention. These components are provided in concentrations and forms known to those in the art.

In some embodiments, the powdered detergent bases of the present invention are prepared by any known preparation methods including spray-drying methods and granulation methods. The detergent base obtained particularly by the spray-drying method and/or spray-drying granulation method are preferred. The detergent base obtained by the spray-drying method is not restricted with respect to preparation conditions. The detergent base obtained by the spray-drying method is the form of hollow granules which are obtained by spraying an aqueous slurry of heat-resistant ingredients, such as surface active agents and builders, into a hot space. After the spray-drying, perfumes, enzymes, bleaching agents, inorganic alkaline builders are added, as desired. With a highly dense, granular detergent base obtained such as by the spray-drying-granulation method, various ingredients may also be added after the preparation of the base.

In some embodiments comprising liquid detergent bases the base is a homogenous solution, while in other embodiments, it is a non-homogenous dispersion.

In some embodiments, the detergent compositions of the present invention are incubated with fabric (e.g., soiled fabrics), in industrial and household uses at temperatures, reaction times and liquor ratios conventionally employed in these environments. The incubation conditions (i.e., the conditions effective for treating materials with detergent compositions according to the present invention), are readily ascertainable by those of skill in the art. Accordingly, the appropriate conditions effective for treatment with the present detergents correspond to those using similar detergent compositions which include wild-type perhydrolase.

As indicated above, in some embodiments of the detergents provided by the present invention are formulated as a pre-wash in the appropriate solution at an intermediate pH, where sufficient activity exists to provide desired improvements in softening, depilling, pilling prevention, surface fiber removal or cleaning. When the detergent composition is a pre-soak (e.g., pre-wash or pre-treatment) composition, either as a liquid, spray, gel or paste composition, the perhydrolase enzyme is generally employed from about 0.00001% to about 5% weight percent based on the total weight of the pre-soak or pre-treatment composition. In such compositions, surfactant(s) may optionally be employed and when employed, is/are generally present at a concentration of from about 0.0005 to about 1 weight percent based on the total weight of the pre-soak. The remainder of the composition comprises conventional components used in the pre-soak (e.g., diluent, buffers, other enzymes (proteases), etc.) at their conventional concentrations.

In some embodiments, the cleaning compositions provided by the present invention find use in cleaning a situs (e.g., a surface or fabric). Typically at least a portion of the situs is contacted with at least one cleaning composition provided herein, in neat form or diluted in a wash liquor, and then the situs is optionally washed and/or rinsed. For purposes of the present invention, washing includes but is not limited to, scrubbing, and mechanical agitation. The fabric comprises most any fabric capable of being laundered in normal consumer use conditions. The cleaning compositions provided herein are typically employed at concentrations of from about 500 ppm to about 15,000 ppm in solution. When the wash solvent is water, the water temperature typically ranges from about 5° C. to about 90° C. and, when the situs comprises a fabric, the water to fabric mass ratio is typically from about 1:1 to about 30:1.

EXPERIMENTAL

The following examples are provided in order to demonstrate and further illustrate certain preferred embodiments and aspects of the present invention and are not to be construed as limiting the scope thereof.

PCT publication WO05/056782 provides methods for the identification and use of perhydrolase enzymes. Each of the Examples in this publication is individually incorporated by reference herein for disclosure of all methods and disclosed therein including but not limited to disclosure of: methods of making perhydrolases, methods of identifying perhydrolases, methods of testing perhydrolases, perhydrolase polynucleotide and polypeptide sequences, methods of using perhydrolases and compositions in which perhydrolases may be employed.

In the experimental disclosure which follows, the following abbreviations apply: ° C. (degrees Centigrade); rpm (revolutions per minute); $H_2O$ (water); HCl (hydrochloric acid); aa (amino acid); by (base pair); kb (kilobase pair); kD (kilodaltons); gm (grams); μg and ug (micrograms); mg (milligrams); ng (nanograms); μl and ul (microliters); ml (milliliters); mm (millimeters); nm (nanometers); μm and um (micrometer); M (molar); mM (millimolar); μM and uM (micromolar); U (units); V (volts); MW (molecular weight); sec (seconds); min(s) (minute/minutes); hr(s) (hour/hours); $MgCl_2$ (magnesium chloride); NaCl (sodium chloride); $OD_{280}$ (optical density at 280 nm); $OD_{600}$ (optical density at 600 nm); PAGE (polyacrylamide gel electrophoresis); EtOH (ethanol); PBS (phosphate buffered saline [150 mM NaCl, 10 mM sodium phosphate buffer, pH 7.2]); SDS (sodium dodecyl sulfate); Tris (tris(hydroxymethyl)aminomethane); TAED (N,N,N'N'-tetraacetylethylenediamine); w/v (weight to volume); v/v (volume to volume); Per (perhydrolase); per (perhydrolase gene); Ms (M. smegmatis); MS (mass spectroscopy); AATCC (American Association of Textile and Coloring Chemists); WFK (wfk Testgewebe GmbH, Bruggen-Bracht, Germany); Amersham (Amersham Life Science, Inc. Arlington Heights, Ill.); Pierce (Pierce Biotechnology, Rockford, Ill.); Amicon (Amicon, Inc., Beverly, Mass.); ATCC (American Type Culture Collection, Manassas, Va.); Amersham (Amersham Biosciences, Inc., Piscataway, N.J.); Becton Dickinson (Becton Dickinson Labware, Lincoln Park, N.J.); BioRad (BioRad, Richmond, Calif.); Clontech (CLONTECH Laboratories, Palo Alto, Calif.); Difco (Difco Laboratories, Detroit, Mich.); GIBCO BRL or Gibco BRL (Life Technologies, Inc., Gaithersburg, Md.); Novagen (Novagen, Inc., Madison, Wis.); Qiagen (Qiagen, Inc., Valencia, Calif.); Invitrogen (Invitrogen Corp., Carlsbad, Calif.); Dionex (Dionex Corp., Sunnyvale, Calif.); Sigma-Aldrich (Sigma-Aldrich Chemical Co., St. Louis, Mo.); Sorvall (Sorvall Instruments, a subsidiary of DuPont Co., Biotechnology Systems, Wilmington, Del.); Stratagene (Stratagene Cloning Systems, La Jolla, Calif.); Roche (Hoffmann La Roche, Inc., Nutley, N.J.); Molecular Devices (Molecular Devices, Corp, Sunnyvale, Calif.); and Agilent (Agilent Technologies, Palo Alto, Calif.).

Example 1

Identification of Perhydrolase Enzymes that Hydrolyze p-Nitrophenylcaproate (pNC6)

As described in PCT publication WO05/056782, the perhydrolase gene of M. smegmatis perhydrolase gene was cloned. The nucleotide sequence of the perhydrolase gene of M. smegmatis perhydrolase gene is:

(SEQ ID NO: 1)

```
ATGGCCAAGCGAATTCTGTGTTTCGGTGATTCCCTGACCTGGGGCTGGGT
CCCCGTCGAAGACGGGGCACCCACCGAGCGGTTCGCCCCCGACGTGCGCT
GGACCGGTGTGCTGGCCCAGCAGCTCGGAGCGGACTTCGAGGTGATCGAG
GAGGGACTGAGCGCGCGCACCACCAACATCGACGACCCCACCGATCCGCG
GCTCAACGGCGCGAGCTACCTGCCGTCGTGCCTCGCGACGCACCTGCCGC
TCGACCTGGTGATCATCATGCTGGGCACCAACGACACCAAGGCCTACTTC
CGGCGCACCCCGCTCGACATCGCGCTGGGCATGTCGGTGCTCGTCACGCA
GGTGCTCACCAGCGCGGGCGGCGTCGGCACCACGTACCCGGCACCCAAGG
TGCTGGTGGTCTCGCCGCCACCGCTGGCGCCCATGCCGCACCCCTGGTTC
CAGTTGATCTTCGAGGGCGGCGAGCAGAAGACCACTGAGCTCGCCCGCGT
GTACAGCGCGCTCGCGTCGTTCATGAAGGTGCCGTTCTTCGACGCGGGTT
CGGTGATCAGCACCGACGGCGTCGACGGAATCCACTTCACCGAGGCCAAC
AATCGCGATCTCGGGGTGGCCCTCGCGGAACAGGTGCGGAGCCTGCTGTA
A
```

The amino acid sequence of the M. smegmatis perhydrolase enzyme is:

(SEQ ID NO: 2)

```
MAKRILCFGDSLTWGWVPVEDGAPTERFAPDVRWTGVLAQQLGADFEVIE
EGLSARTTNIDDPTDPRLNGASYLPSCLATHLPLDLVIIMLGTNDTKAYF
RRTPLDIALGMSVLVTQVLTSAGGVGTTYPAPKVLVVSPPPLAPMPHPWF
QLIFEGGEQKTTELARVYSALASFMKVPFFDAGSVISTDGVDGIHFTEAN
NRDLGVALAEQVRSLL.
```

Also, as described in PCT publication WO05/056782 each and every amino acid position of the M. smegmatis perhydrolase enzyme was mutated to each of the remaining 19 amino acids produce a site saturation library. Using the methods described in Example 2 of PCT publication WO05/056782, the wild-type perhydrolase each and of the perhydrolase variants in the site saturation library was tested for its ability to hydrolyze p-nitrophenylcaproate, a $C_6$ acyl ester substrate.

Wild type perhydrolase was not able to hydrolyze pNC6. The following perhydrolase variants were identified as having an ability to hydrolyze pNC6:

TABLE 1

Perhydrolase variants able to hydrolyze pNC6

| Wild-Type Residue/Position | Amino Acid Variant(s) |
|---|---|
| L12 | G, P, Q |
| G22 | W |
| N59 | P |
| I153 | P |
| F154 | Q, S, T, V |
| I194 | G |
| F196 | S, Q, V, G, P, I, H |
| L204 | Y, W |

Example 2

Production and Screening of Combinatorial Libraries

The mutations identified in Table 1 were combined together to produce four different libraries, NSAL1, NSAL2, NSAL3 and NSAL4 using wild-type perhydrolase (SEQ ID NO:2) and the L12G variant as parent molecules. The primers used to make the combinatorial libraries are as follows, where to the "NNS" sequence represents a degenerate codon NNG/C (N=G, A, T or C) that encodes all 20 amino acids and one stop codon:

TABLE 2

Mutations and Primers Used for Combinatorial Libraries

| Mutations | Primer Sequence | |
|---|---|---|
| L12G | GTGTTTCGGTGATTCCGGCACCTG GGGCTGGGTCC | (SEQ ID NO: 3) |
| L12P | GTGTTTCGGTGATTCCCCGACCTG GGGCTGGGTCCC | (SEQ ID NO: 4) |
| L12Q | GTGTTTCGGTGATTCCCAGACCTG GGGCTGGGTCCC | (SEQ ID NO: 5) |
| L12NNS | GTGTTTCGGTGATTCCNNSACCTG GGGCTGGGTCC | (SEQ ID NO: 6) |
| I194G | GACGGCGTCGACGGAGGCCACTTC ACCGAGGCCAAC | (SEQ ID NO: 7) |
| I194NNS | GACGGCGTCGACGGANNSCACTTC ACCGAGGCCAAC | (SEQ ID NO: 8) |
| F154T | TGGTTCCAGTTGATCACCGAGGGC GGCGAGCAGAAG | (SEQ ID NO: 9) |
| F154S | TGGTTCCAGTTGATCAGCGAGGGC GGCGAGCAGAAG | (SEQ ID NO: 10) |
| F154NNS | TGGTTCCAGTTGATCNNSGAGGGC GGCGAGCAGAAG | (SEQ ID NO: 11) |
| F196S | GCGTCGACGGAATCCACAGCACCG AGGCCAACAATCG | (SEQ ID NO: 12) |
| F196Q | GCGTCGACGGAATCCACCAGACCG AGGCCAACAATCG | (SEQ ID NO: 13) |
| F196V | GCGTCGACGGAATCCACGTTACCG AGGCCAACAATCG | (SEQ ID NO: 14) |
| F196G | GCGTCGACGGAATCCACGGTACCG AGGCCAACAATCG | (SEQ ID NO: 15) |
| F196P | GCGTCGACGGAATCCACCCGACCG AGGCCAACAATCG | (SEQ ID NO: 16) |
| F1961 | GCGTCGACGGAATCCACATCACCG AGGCCAACAATCG | (SEQ ID NO: 17) |
| F196NNS | GCGTCGACGGAATCCACNNSACCG AGGCCAACAATCG | (SEQ ID NO: 18) |
| F154V | TGGTTCCAGTTGATCGTTGAGGGC GGCGAGCAGAAG | (SEQ ID NO: 19) |
| F196H | GCGTCGACGGAATCCACCATACCG AGGCCAACAATCG | (SEQ ID NO: 20) |
| F154Q | TGGTTCCAGTTGATCCAGGAGGGC GGCGAGCAGAAG | (SEQ ID NO: 21) |
| N59P | AGCGCGCGCACCACCCCGATCGAC GACCCCACCGATC | (SEQ ID NO: 22) |

TABLE 2-continued

Mutations and Primers Used for Combinatorial Libraries

| Mutations | Primer Sequence | |
|---|---|---|
| L204Y | GCCAACAATCGCGATTATGGGGTG GCCCTCGCGGAAC | (SEQ ID NO: 23) |
| L204W | GCCAACAATCGCGATTGGGGGGTG GCCCTCGCGGAAC | (SEQ ID NO: 24) |
| L204NNS | GCCAACAATCGCGATNNSGGGGTG GCCCTCGCGGAAC | (SEQ ID NO: 25) |
| I153P | CCCTGGTTCCAGTTGCCGTTCGAG GGCGGCGAGCAG | (SEQ ID NO: 26) |
| G22W | GTCCCCGTCGAAGACTGGGCACCC ACCGAGCGGTTC | (SEQ ID NO: 27) |

QuikChange multi site-directed mutagenesis (QCMS) was used to create combinatorial libraries NSAL1-NSAL4 using method described in WO 05/056782. The QCMS reaction consisted of 16.5 uL of sterile distilled H2O, 2.5 uL of 10×buffer from the kit, 1 uL dNTPs from the kit, 3 uL of the 20 primers mix (10 uL of each 100 ng/uL primer was mixed together ahead of time), 1 uL of pMSAT-NcoI miniprep DNA as template (~50 ng), and 1 uL of the enzyme blend from the kit for a total of 25 uL. The cycling conditions were 95° C. for 1 mM once, 95° C. for 1 min, 55° C. for 1 mM, 65° C. for 10 min for 30 cycles. Next, DpnI digestion was carried out twice sequentially with 1 or 0.5 uL of enzyme (QCMS kit) at 37° C. for 4 hours. 2 uL of the reaction was transformed into BL21 (DE3) pLysS competent cells (Novagen) as per the manufacturer's instructions. The transformation was plated on LB plates containing 100 ppm carbenicillin, 0.1 mM IPTG and 0.25% of tricaproin (a $C_6$ acyl chain substrate that was mixed in the media by sonication).

After incubation of the plates at 37° C. for 24 hours followed by room temperature for 2 days, a majority of the halo-forming colonies were grown overnight at 37° C. in 96-well plates containing LB with 100 ppm of carbenicillin. To re-assess the halo-formers, the cultures were replica-stamped onto a large agar plate containing LB, 100 ppm carbenicillin, 0.1 mM IPTG and 0.25% of tricaproin.

Table 3 describes further details of the combinatorial libraries and their screening.

TABLE 3

Description of Libraries and Colonies Screened

| LIBRARY | PRIMERS USED | PARENT MOLECULE | COLONIES SCREENED | COLONIES WITH HALOS** |
|---|---|---|---|---|
| NSAL1 | L12NNS, F154NNS, F196NNS, I194NNS, L204NNS | WILD TYPE | 182 | 21 |
| NSAL2 | L12NNS, F154NNS, F196NNS, I194NNS, L204NNS | L12G | 169 | 40 |
| NSAL3 | All primers in Table 1 except NNS codon primers | WILD TYPE | ~1200* | 4 |
| NSAL4 | All primers in Table 1 except NNS codon primers | L12G | ~1000* | ~100-200* |

*This number is approximate. The exact number of colonies was not determined.

**Some of the halo forming colonies did not form halos upon re-testing. The number of halo-formers in NSAL2 and NSAL4 is higher than in NSAL1 and NSAL3 due to the L12G parent that was the present in 25% of the NSAL2 and NSAL4 libraries.

The polynucleotides encoding the perhydrolase enzyme of the halo-forming colonies were sequenced to determine which mutations contribute to halo formation (Table 4).

TABLE 4

Sequence of Halo-Forming Clones*

| LIBRARY | SEQUENCE |
|---|---|
| NSAL1 | I194G (3 clones) |
| NSAL3 | I194G |
| NSAL4 | L12G G22W |
| NSAL2 | L12G I194M |
| NSAL1 | F154A I194M (2 clones) |
| NSAL1 | F154A |
| NSAL1 | F154G I194V |
| NSAL1 | F154E I194S (3 clones) |
| NSAL1 | F154E |
| NSAL3 | F154T F196I (2 clones) |
| NSAL3 | F154V |
| NSAL3 | L12Q F154V |
| NSAL3 | L12M F154E |
| NSAL3 | L12G F154G I194V |

*Halo-producing L12G clones are not listed in the table, since this mutation was known to produce halos on tricaproin plates.

Example 3

Biochemical Characterization of Halo-Forming Variants

Variants that formed halos on tricaproin plates that had an amino acid sequence different from a parent sequence were tested for their ability to hydrolyze p-nitrophenylcaproate (pNC6) and p-nitrophenyloctanoate (pNC8) in 100 mM Tris/HCl pH 8, 0.1% Triton-X100 and 1 mM of the pNC6 or pNC8 using methods described in Example 2 of PCT publication WO 05/056782.

The rate of p-nitrophenol appearance was recorded for each of the halo-forming variants. The wild type enzyme showed no hydrolysis of pNC6 or pNC8. Ratios of hydrolysis of pNC6/pNC8 are shown in Table 5 below.

TABLE 5

Variants having pNC6/pNC8 Hydrolytic Activity

| Sequences | Ratio pNC6 Hydrolysis:pNC8 Hydrolysis |
|---|---|
| F154A I194M | 1.13 |
| F154G I194V | 0.34 |
| L12G | 0.79 |
| L12G I194M | 0.65 |

Variants F154T F1961,L12Q F154V, L12M F154E, L12G F154G, F154E I194S, and L12G G22W had the ability to hydrolyze tricaproin but did not hydrolyze pNC6 or pNC8.

The data show that specific variants of the M. smegmatis perhydrolase are capable of using medium and long chain acyl esters as a substrate.

Example 4

Enzyme Analysis

In this Example, methods that find use in assessing enzyme purity and activity are described. However, it is not intended that the present invention be limited to these specific methods, as other suitable methods find use.

Enzyme Activity Assay (pNB Assay)

This activity is measured by hydrolysis of p-nitrophenylbutyrate or other long chain p-nitrophenyl compounds. The reaction mixture was prepared by adding 10 ul of 100 mM p-nitrophenylbutyrate in dimethylsulfoxide to 990 ml of 100 mM Tris-HCl buffer, pH 8.0 containing 0.1% Triton X-100. The background rate of hydrolysis was measured before the addition of enzyme at 410 nm. The reaction was initiated by the addition of 10 ul of enzyme to 990 ml of the reaction and the change of absorbance at 410 nm was measured at room temperate (~23° C.). The background corrected results are reported as $\delta A_{410}$/min/ml or $\delta A_{410}$/min/mg protein.

Transesterification

Transesterification is measured by GC separation of products in buffered aqueous reactions. Reactions to measure ethyl acetate transesterification with propanol contained in 1 ml of 50 mM KPO4, pH 7.0; 200 mM ethyl acetate, 200 mM 1-propanol, and enzyme. Reactions to measure ethyl acetate transesterification with neopentyl glycol (NPG) contained in 1 ml of 50 mM KPO4, pH 7.0; 303 mM ethyl acetate, 100 mM NPG, and enzyme. The reactions were incubated at the indicated temperatures and for the indicated times. Separations are performed using a 30M FFAP column (Phenomenex). The inlet split ratio was approximately 1:25, the injector is 250° C., head pressure of 10 psi He, and detection was by FID at 250° C. The chromatography program was set at 40° C. initial for 4 min, followed by a gradient of 15° C./min to 180° C. Components eluted in the following order and were not quantified; ethyl acetate, ethyl alcohol, propyl acetate, propyl alcohol, acetic acid, NPG diacetate, NPG monoacetate, and NPG.

Preparation of Substrate

The substrates were prepared as described herein. Ethyl acetate (EtOAc) or other water soluble esters were diluted in a desired buffer to a concentration of 10 mM of ester. tributyrin and other water insoluble substrates are prepared by making substrate swatches. Polyester swatches were cut from non-dyed polyester fabric (Polycotton, PCW 22) using a ⅝ inch punch and placed in a 24-well microtiter plate (Costar, Cell Culture Plate). The insoluble ester was diluted to 1.03 M in hexane. Then, 10 μL of the insoluble ester solution were then adsorbed onto the polyester swatch.

Determination of Hydrolysis (GC Assay)

The hydrolytic assay described below finds use in determining the amount of substrate hydrolysis. In this assay, the assay solution was comprised of 50 mM potassium phosphate pH 7.5, 10 mM ester substrate, 29 mM hydrogen peroxide, and 20 mM potassium chloride in a total volume of 0.99 ml and an amount of enzyme that would generate 20 nmoles of acetic acid per minute at 25° C.

For measuring water insoluble ester hydrolysis, the reaction mixture was added to the insoluble ester fabric swatch. The swatch was prepared as described above ("Preparation of Substrate"). All the other conditions for the assay were the same except for exclusion of other ester substrates.

Hydrolytic activity was measured by monitoring the increase of acids generated by the enzyme from acyl donor substrates using gas chromatography coupled with flame ionization detection. The assay was conducted by first pipetting 50 μL of assay solution containing all the components except the enzyme into 200 μL of methanol (HPLC grade) to determine the amount of acid in the assay solution at time 0. Then, 10 μL of enzyme was added to the assay solution to a desired final concentration which produced approximately 20 nanomoles of acid per minute. A timer was started and 50 μL aliquots were taken from the assay solution and added to 200 μL of methanol at various times, typically 2, 5, 10, 15, 25, 40, and 60 minutes, after addition of the enzyme.

These methanol-quenched samples were then injected into a gas chromatograph coupled with a flame ionization detector (Agilent 6890N) and analyzed for hydrolytic components, acetic, and butyric acids, etc. Gas chromatography was conducted using a nitroterephthalic acid modified polyethylene glycol column (Zebron FFAP; with dimensions: 30 m long, 250 um diameter, 250 nm film thickness). A 3 μL aliquot of sample was applied to the column by a splitless injection under constant a helium flow of 1.0 mL/minute. The inlet was maintained at a temperature of 250° C., and was purged of any remaining sample components after 2 minutes. When analyzing acetic acid, the temperature of the column was maintained at 75° C. for 1 minute after injection, increased 25° C./minute to 100° C., then increased 15° C./minute to 200° C.

When analyzing butyric acid, the temperature of the column was controlled as described above, except the temperature was additionally increased 25° C./minute to 225° C. and held at 225° C. for 1 minute. The flame ionization detector was maintained throughout the chromatography at 250° C. and under constant hydrogen flow of 25 mL/minute, air flow of 200 mL/minute, and a combined column and makeup helium flow of 30 mL/minute. The amount of hydrolyzed acid in the sample was then determined by integrating the acid peak in the chromatogram for total ion counts and calculating the acid from the ion count using a standard curve generated under the above conditions for acetic and butyric acids at varying concentrations in the assay solution (without enzyme).

Determination of Perhydrolysis (OPD Assay)

The perhydrolytic activity assay described below finds use in determining the amount of peracid formed in the reaction. In these assays, the solution comprised 50 mM potassium phosphate pH 7.5, 10 mM ester substrate, 29 mM hydrogen peroxide, 20 mM potassium chloride, and 10 mM O-phenylenediamine When using water insoluble ester as the acyl donor, an ester-adsorbed fabric swatch was used as the substrate, prepared as described above ("Preparation of Substrate").

Perhydrolytic activity was measured by monitoring the absorbance increase at 458 nm of oxidized o-phenylenediamine (OPD) by peracid generated with the enzyme. The perhydrolytic activity assay solution was prepared in the same manner as the hydrolytic activity assay solution, except that OPD was added to the assay solution to a final concentration of 10 mM. The OPD solution was prepared immediately before conducting the assay by dissolving 72 mg OPD (Sigma-Aldrich, dihydrochloride) in 19.94 mL of the same buffer and the pH was adjusted by slowly adding 60 μL of 13.5 M potassium hydroxide. The pH was measured and if needed, small quantities of potassium hydroxide were added to return the pH to the original pH of the buffer. Then, 495 μL of this OPD solution were added with the other assay components to a final assay volume of 0.990 mL. An assay quenching solution was also prepared by dissolving 36 mg OPD in 20 mL 100 mM citric acid and 70% ethanol.

The assay was typically conducted at 25° C. The assay was started by pipetting 100 μL of assay solution before the addition of the enzyme into 200 μL of quenching solution to determine the amount of perhydrolytic components and background absorbance in the assay solution at time 0. Then, 10 μL of enzyme were added to the assay solution to a desired final concentration which produced approximately 10 nanomoles of peracid per minute. A timer was started and 100 μL aliquots were taken from the assay solution and added to 200 μL of quenching solution at various times, typically 2, 5, 10, 15, 25, 40, and 60 minutes, after adding the enzyme. The quenched assay solutions were incubated for 30 minutes to allow any remaining peracid to oxidize the OPD. Then, 100 μL of each quenched assay solution was transferred to a 96-well microtiter plate (Costar) and the absorbance of the solution was measured at 458 nm by a spectrophotometric plate reader (Molecular Devices, SpectraMAX 250). The amount of peracid in each quenched sample was calculated using a standard curve generated under the above conditions with peracetic acid at varying concentrations in the assay solution (without enzyme).

Perhydrolysis/Hydrolysis Ratio:

Perhydrolysis/Hydrolysis ratio=Perhydrolysis measured in the Perhydrolysis assay/(Total acid detected in the hydrolysis assay−Perhydrolysis measured in the perhydrolysis assay)

Perhydrolase Peracid Generation Assay

For perhydrolysis measurements, the enzyme is incubated in the buffer of choice at a specified temperature with a substrate ester in the presence of hydrogen peroxide. Typical substrates to measure perhydrolysis of medium or long chain esters include methyl or ethyl esters of hexanoate, heptanoate, octanoate, nonanoate or C10-C22 or longer fatty acid esters, and others. In addition, the wild type enzyme was found able to hydrolyze nitrophenylesters of short chain acids. The latter are convenient substrates to measure enzyme concentration. In some embodiments, peracid acid and acetic acid are measured by the ABTS or HPLC assays. Nitrophenylester hydrolysis is also described below.

ARTS Assay (One Milliliter):

This assay provides a determination of peracetic acid produced by perhydrolase. This protocol was adapted from Karst et al. (Karst et al., Analyst, 122:567-571 [1997]). Briefly, a 100 μL aliquot of solution to be analyzed was added to 1 mL 125 mM $K^+$ citrate pH 5, 1 mM ABTS, 50 μM KI. Absorbance was measured at 420 nm for highest sensitivity. However, multiple additional wavelengths were sometimes used over the broad absorption spectrum of ABTS. Calibration curves were constructed based on known peracid concentration series.

HPLC (Model—Agilent 1100) Determination of Perhydrolase Reaction Products:

For determination of the ratio of perhydrolysis to hydrolysis of the perhydrolase reaction, perhydrolase reaction samples were quenched by acidification to a final concentration of 0.24% methanesulfonic acid, and the products were separated by reverse phase HPLC on a Dionex OA column (cat #062903; Dionex). The mobile phase was 100 mM $NaPO_4$, pH 3.9 (buffer was prepared by titrating 100 mM $Na_2PO_4$ with methanesulfonic acid to pH 3.9) run under isocratic conditions at 30° C. Detection was at 210 nm. Concentrations of products were calculated by comparison of the integrated peak areas against calibration standards.

Nitrophenylester Hydrolysis Kinetic Assay

Enzyme and substrate were incubated in 100 mM Tris/HCl pH 8.0 (or 50 mM $B(OH)_3$ pH 9.5 or another buffer). Absorbance at 402 nm was monitored. In some experiments, the assay was carried out in standard 1 mL cuvettes, while in other experiments, microtiter plate wells were used. The latter method was used for the screening of mutant libraries. Enzyme concentration was determined by comparison to standard curves obtained under the same reaction conditions.

Para-Nitrophenylcaproate Hydrolysis Assay

The pNC6 substrate solution was prepared by mixing 1 mM pNC6 (100 mM stock solution), 1 ml DMSO, 19 ml 100 mM Phosphate (pH8), and glycerol to a final concentration of 10%. To assay samples, 10 μl of the cell lysate were added to 190 μl of the substrate solution, and assayed at 405 nm for 15 minutes in a spectrophotometer. The results were presented as the average of two experiments.

Para-Pitrophenyl Acetate (pNA) Hydrolysis Assay

Aliquots of the lysed cell supernatant were diluted 1-100 in 100 mM phosphate buffer (pH 8). To assay the samples, 5 μl of the 1-100 diluted cell supernatant were placed into each well of a microtiter plate. Then, 195 μl of reaction buffer/substrate mix (1 mM pNA, 100 mM phosphate, pH 8, 10% glycerol) were added, and the absorbance rate at 405 nm measured over 3 minutes (kinetics program, microtiter plate reader). The results were presented as the average of two experiments.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

Having described the preferred embodiments of the present invention, it will appear to those ordinarily skilled in the art that various modifications may be made to the disclosed embodiments, and that such modifications are intended to be within the scope of the present invention.

Those of skill in the art readily appreciate that the present invention is well adapted to carry out the objects and obtain the ends and advantages mentioned, as well as those inherent therein. The compositions and methods described herein are representative of preferred embodiments, are exemplary, and are not intended as limitations on the scope of the invention. It is readily apparent to one skilled in the art that varying substitutions and modifications may be made to the invention disclosed herein without departing from the scope and spirit of the invention.

The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

SEQUENCE LISTING

```
<160> NUMBER OF SEQ ID NOS: 31

<210> SEQ ID NO 1
<211> LENGTH: 651
<212> TYPE: DNA
<213> ORGANISM: Mycobacterium smegmatis

<400> SEQUENCE: 1

atggccaagc gaattctgtg tttcggtgat tccctgacct ggggctgggt ccccgtcgaa      60

gacggggcac ccaccgagcg gttcgccccc gacgtgcgct ggaccggtgt gctggcccag     120

cagctcggag cggacttcga ggtgatcgag gagggactga gcgcgcgcac caccaacatc     180

gacgacccca ccgatccgcg gctcaacggc gcgagctacc tgccgtcgtg cctcgcgacg     240

cacctgccgc tcgacctggt gatcatcatg ctgggcacca acgacaccaa ggcctacttc     300

cggcgcaccc cgctcgacat cgcgctgggc atgtcggtgc tcgtcacgca ggtgctcacc     360

agcgcgggcg gcgtcggcac cacgtacccg gcacccaagg tgctggtggt ctcgccgcca     420

ccgctggcgc ccatgccgca cccctggttc cagttgatct tcgagggcgg cgagcagaag     480

accactgagc tcgcccgcgt gtacagcgcg ctcgcgtcgt tcatgaaggt gccgttcttc     540

gacgcgggtt cggtgatcag caccgacggc gtcgacggaa tccacttcac cgaggccaac     600

aatcgcgatc tcggggtggc cctcgcggaa caggtgcgga gcctgctgta a              651


<210> SEQ ID NO 2
<211> LENGTH: 216
<212> TYPE: PRT
<213> ORGANISM: Mycobacterium smegmatis

<400> SEQUENCE: 2

Met Ala Lys Arg Ile Leu Cys Phe Gly Asp Ser Leu Thr Trp Gly Trp
1               5                   10                  15
```

```
Val Pro Val Glu Asp Gly Ala Pro Thr Glu Arg Phe Ala Pro Asp Val
            20                  25                  30

Arg Trp Thr Gly Val Leu Ala Gln Gln Leu Gly Ala Asp Phe Glu Val
        35                  40                  45

Ile Glu Glu Gly Leu Ser Ala Arg Thr Thr Asn Ile Asp Asp Pro Thr
    50                  55                  60

Asp Pro Arg Leu Asn Gly Ala Ser Tyr Leu Pro Ser Cys Leu Ala Thr
65                  70                  75                  80

His Leu Pro Leu Asp Leu Val Ile Ile Met Leu Gly Thr Asn Asp Thr
                85                  90                  95

Lys Ala Tyr Phe Arg Arg Thr Pro Leu Asp Ile Ala Leu Gly Met Ser
            100                 105                 110

Val Leu Val Thr Gln Val Leu Thr Ser Ala Gly Gly Val Gly Thr Thr
        115                 120                 125

Tyr Pro Ala Pro Lys Val Leu Val Val Ser Pro Pro Pro Leu Ala Pro
    130                 135                 140

Met Pro His Pro Trp Phe Gln Leu Ile Phe Glu Gly Gly Glu Gln Lys
145                 150                 155                 160

Thr Thr Glu Leu Ala Arg Val Tyr Ser Ala Leu Ala Ser Phe Met Lys
                165                 170                 175

Val Pro Phe Phe Asp Ala Gly Ser Val Ile Ser Thr Asp Gly Val Asp
            180                 185                 190

Gly Ile His Phe Thr Glu Ala Asn Asn Arg Asp Leu Gly Val Ala Leu
        195                 200                 205

Ala Glu Gln Val Arg Ser Leu Leu
    210                 215


<210> SEQ ID NO 3
<211> LENGTH: 35
<212> TYPE: DNA
<213> ORGANISM: Artificial Sequence
<220> FEATURE:
<223> OTHER INFORMATION: primer

<400> SEQUENCE: 3

gtgtttcggt gattccggca cctggggctg ggtcc                                35


<210> SEQ ID NO 4
<211> LENGTH: 36
<212> TYPE: DNA
<213> ORGANISM: Artificial Sequence
<220> FEATURE:
<223> OTHER INFORMATION: primer

<400> SEQUENCE: 4

gtgtttcggt gattccccga cctggggctg ggtccc                               36


<210> SEQ ID NO 5
<211> LENGTH: 36
<212> TYPE: DNA
<213> ORGANISM: Artificial Sequence
<220> FEATURE:
<223> OTHER INFORMATION: primer

<400> SEQUENCE: 5

gtgtttcggt gattcccaga cctggggctg ggtccc                               36


<210> SEQ ID NO 6
<211> LENGTH: 35
<212> TYPE: DNA
```

<213> ORGANISM: Artificial Sequence
<220> FEATURE:
<223> OTHER INFORMATION: primer
<220> FEATURE:
<221> NAME/KEY: misc_feature
<222> LOCATION: (17)..(18)
<223> OTHER INFORMATION: n is a, c, g, or t

<400> SEQUENCE: 6 gtgtttcggt gattccnnsa cctggggctg ggtcc 35

<210> SEQ ID NO 7
<211> LENGTH: 36
<212> TYPE: DNA
<213> ORGANISM: Artificial Sequence
<220> FEATURE:
<223> OTHER INFORMATION: primer

<400> SEQUENCE: 7 gacggcgtcg acggaggcca cttcaccgag gccaac 36

<210> SEQ ID NO 8
<211> LENGTH: 36
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (16)..(17)
<223> OTHER INFORMATION: n is a, c, g, or t

<400> SEQUENCE: 8 gacggcgtcg acggannsca cttcaccgag gccaac 36

<210> SEQ ID NO 9
<211> LENGTH: 36
<212> TYPE: DNA
<213> ORGANISM: Artificial Sequence
<220> FEATURE:
<223> OTHER INFORMATION: primer

<400> SEQUENCE: 9 tggttccagt tgatcaccga gggcggcgag cagaag 36

<210> SEQ ID NO 10
<211> LENGTH: 36
<212> TYPE: DNA
<213> ORGANISM: Artificial Sequence
<220> FEATURE:
<223> OTHER INFORMATION: primer

<400> SEQUENCE: 10 tggttccagt tgatcagcga gggcggcgag cagaag 36

<210> SEQ ID NO 11
<211> LENGTH: 36
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (16)..(17)
<223> OTHER INFORMATION: n is a, c, g, or t

<400> SEQUENCE: 11 tggttccagt tgatcnnsga gggcggcgag cagaag 36

<210> SEQ ID NO 12
<211> LENGTH: 37
<212> TYPE: DNA
<213> ORGANISM: Artificial Sequence
<220> FEATURE:
<223> OTHER INFORMATION: primer

<400> SEQUENCE: 12 gcgtcgacgg aatccacagc accgaggcca acaatcg 37

<210> SEQ ID NO 13
<211> LENGTH: 37
<212> TYPE: DNA
<213> ORGANISM: Artificial Sequence
<220> FEATURE:
<223> OTHER INFORMATION: primer

<400> SEQUENCE: 13 gcgtcgacgg aatccaccag accgaggcca acaatcg 37

<210> SEQ ID NO 14
<211> LENGTH: 37
<212> TYPE: DNA
<213> ORGANISM: Artificial Sequence
<220> FEATURE:
<223> OTHER INFORMATION: primer

<400> SEQUENCE: 14 gcgtcgacgg aatccacgtt accgaggcca acaatcg 37

<210> SEQ ID NO 15
<211> LENGTH: 37
<212> TYPE: DNA
<213> ORGANISM: Artificial Sequence
<220> FEATURE:
<223> OTHER INFORMATION: primer

<400> SEQUENCE: 15 gcgtcgacgg aatccacggt accgaggcca acaatcg 37

<210> SEQ ID NO 16
<211> LENGTH: 37
<212> TYPE: DNA
<213> ORGANISM: Artificial Sequence
<220> FEATURE:
<223> OTHER INFORMATION: primer

<400> SEQUENCE: 16 gcgtcgacgg aatccacccg accgaggcca acaatcg 37

<210> SEQ ID NO 17
<211> LENGTH: 37
<212> TYPE: DNA
<213> ORGANISM: Artificial Sequence
<220> FEATURE:
<223> OTHER INFORMATION: primer

<400> SEQUENCE: 17 gcgtcgacgg aatccacatc accgaggcca acaatcg 37

<210> SEQ ID NO 18
<211> LENGTH: 37
<212> TYPE: DNA
<213> ORGANISM: Artificial Sequence
<220> FEATURE:
<223> OTHER INFORMATION: primer
<220> FEATURE:

<221> NAME/KEY: misc_feature
<222> LOCATION: (18)..(19)
<223> OTHER INFORMATION: n is a, c, g, or t

<400> SEQUENCE: 18 gcgtcgacgg aatccacnns accgaggcca acaatcg 37

<210> SEQ ID NO 19
<211> LENGTH: 36
<212> TYPE: DNA
<213> ORGANISM: Artificial Sequence
<220> FEATURE:
<223> OTHER INFORMATION: primer

<400> SEQUENCE: 19 tggttccagt tgatcgttga gggcggcgag cagaag 36

<210> SEQ ID NO 20
<211> LENGTH: 37
<212> TYPE: DNA
<213> ORGANISM: Artificial Sequence
<220> FEATURE:
<223> OTHER INFORMATION: primer

<400> SEQUENCE: 20 gcgtcgacgg aatccaccat accgaggcca acaatcg 37

<210> SEQ ID NO 21
<211> LENGTH: 36
<212> TYPE: DNA
<213> ORGANISM: Artificial Sequence
<220> FEATURE:
<223> OTHER INFORMATION: primer

<400> SEQUENCE: 21 tggttccagt tgatccagga gggcggcgag cagaag 36

<210> SEQ ID NO 22
<211> LENGTH: 37
<212> TYPE: DNA
<213> ORGANISM: Artificial Sequence
<220> FEATURE:
<223> OTHER INFORMATION: primer

<400> SEQUENCE: 22 agcgcgcgca ccaccccgat cgacgacccc accgatc 37

<210> SEQ ID NO 23
<211> LENGTH: 37
<212> TYPE: DNA
<213> ORGANISM: Artificial Sequence
<220> FEATURE:
<223> OTHER INFORMATION: primer

<400> SEQUENCE: 23 gccaacaatc gcgattatgg ggtggccctc gcggaac 37

<210> SEQ ID NO 24
<211> LENGTH: 37
<212> TYPE: DNA
<213> ORGANISM: Artificial Sequence
<220> FEATURE:
<223> OTHER INFORMATION: primer

<400> SEQUENCE: 24 gccaacaatc gcgattgggg ggtggccctc gcggaac 37

<210> SEQ ID NO 25
<211> LENGTH: 37
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (16)..(17)
<223> OTHER INFORMATION: n is a, c, g, or t

<400> SEQUENCE: 25 gccaacaatc gcgatnnsgg ggtggccctc gcggaac 37

<210> SEQ ID NO 26
<211> LENGTH: 36
<212> TYPE: DNA
<213> ORGANISM: Artificial Sequence
<220> FEATURE:
<223> OTHER INFORMATION: primer

<400> SEQUENCE: 26 ccctggttcc agttgccgtt cgagggcggc gagcag 36

<210> SEQ ID NO 27
<211> LENGTH: 36
<212> TYPE: DNA
<213> ORGANISM: Artificial Sequence
<220> FEATURE:
<223> OTHER INFORMATION: primer

<400> SEQUENCE: 27 gtccccgtcg aagactgggc acccaccgag cggttc 36

<210> SEQ ID NO 28
<211> LENGTH: 4
<212> TYPE: PRT
<213> ORGANISM: Artificial Sequence
<220> FEATURE:
<223> OTHER INFORMATION: engineered peptide

<400> SEQUENCE: 28

Gly Asp Ser Leu
1

<210> SEQ ID NO 29
<211> LENGTH: 4
<212> TYPE: PRT
<213> ORGANISM: Artificial Sequence
<220> FEATURE:
<223> OTHER INFORMATION: engineered peptide

<400> SEQUENCE: 29

Gly Arg Thr Thr
1

<210> SEQ ID NO 30
<211> LENGTH: 4
<212> TYPE: PRT
<213> ORGANISM: Artificial Sequence
<220> FEATURE:
<223> OTHER INFORMATION: engineered peptide

<400> SEQUENCE: 30

Ala Arg Thr Thr
1

-continued

```
<210> SEQ ID NO 31
<211> LENGTH: 4
<212> TYPE: PRT
<213> ORGANISM: Artificial Sequence
<220> FEATURE:
<223> OTHER INFORMATION: engineered peptide

<400> SEQUENCE: 31

Ser Gly Asn His
1
```

We claim:

1. An isolated perhydrolase enzyme, *comprising:*

*an amino acid substitution at position 204; or*

*amino acid substitutions at positions 12 and 22, 12 and 154, 12 and 194, 154 and 194, or 154 and 196;* wherein said enzyme perhydrolyzes long chain acyl ester substrates of at least six carbon atoms[.]*; the amino acid positions are positionally equivalent to those in M. smegmatis perhydrolase having the amino acid sequence of SEQ ID NO: 2;* and [wherein] the amino acid sequence of said enzyme is at least 90% identical to the amino acid sequence of the wild type perhydrolase of M. smegmatis, as set forth in SEQ ID NO: 2.

2. The isolated perhydrolase enzyme of claim 1, wherein said enzyme produces long chain peracid in the presence of a long chain acyl ester substrate and peroxide.

3. The isolated perhydrolase enzyme of claim 1, wherein said long chain acyl ester substrate contains a chain of at least nine carbon atoms.

[4. The isolated perhydrolase enzyme of claim 1, wherein said enzyme comprises at least one substitution at an amino acid position equivalent to a position in M. smegmatis perhydrolase comprising the amino acid sequence set forth in SEQ ID NO:2, wherein said at least one substitution is selected from positions 12, 22, 59, 153, 154, 194, 196, and 204.]

[5. The isolated perhydrolase enzyme of claim 4, wherein said enzyme comprises at least one of the following amino acid substitutions: a Gly, Pro or Gln at position 12, a Trp at position 22, a Pro at position 59, a Pro at position 153, a Thr, Ser, Val or Gin at position 154, a Gly at position 194, a Ser, Gln Val, Gly, Pro, Ile or His at position 196, a Tyr or Trp at position 204, or any combination thereof, wherein said amino acid positions are positionally equivalent to positions 12, 22, 59, 153, 154, 194, 196 and 204 in the M. smegmatis perhydrolase of SEQ ID NO:2.]

[6. The isolated perhydrolase enzyme of claim 1, wherein said enzyme comprises at least one of the following amino acid substitutions: anAla at position 154 and a Met at position 194, a Gly at position 154 and a Val at position 194, or a Gly at position 12 and a Met at position 194, wherein said amino acid positions are positionally equivalent to positions 12, 154 and 194 in the M. smegmatis perhydrolase of SEQ ID NO:2.]

7. The isolated perhydrolase enzyme of claim 1, wherein said enzyme has a perhydrolysis to hydrolysis ratio of greater than 1.

8. The isolated perhydrolase enzyme of claim 1, wherein said enzyme has a peracid hydrolysis rate that is lower than the peracid hydrolysis rate of SEQ ID NO:2.

[9. An isolated perhydrolase enzyme, wherein said enzyme hydrolyzes long chain acyl ester substrates of at least six carbon atoms, and wherein the amino acid sequence of said enzyme is at least 90% identical to the amino acid sequence of the wild type perhydrolase of M. smegmatis, as set forth in SEQ ID NO: 2.]

[10. The isolated perhydolase enzyme of claim 9, wherein said enzyme produces long chain peracid in the presence of a long chain acyl ester substrate and peroxide.]

[11. The isolated perhydrolase enzyme of claim 9, wherein said long chain acyl ester substrate contains a chain of at least nine carbon atoms.]

12. A cleaning composition comprising the perhydrolase enzyme of claim 1.

13. The cleaning composition of claim 12, wherein said composition further comprises a long chain acyl ester substrate and a source of peroxide.

14. The cleaning composition of claim 13, wherein said composition further comprises a surfactant.

15. The cleaning composition of claim 12, wherein said composition is a laundry detergent.

16. A cleaning method comprising contacting a substrate in the presence of the cleaning composition of claim 12 to clean said substrate.

* * * * *